United States Patent [19]

Hemmerle et al.

[11] Patent Number: 5,463,062
[45] Date of Patent: Oct. 31, 1995

[54] SUBSTITUTED CYCLOHEXANE DERIVATIVES, PROCESSES FOR THEIR PREPARATION AND THE USE OF THE COMPOUNDS FOR TREATING DISEASES

[75] Inventors: Horst Hemmerle, Lorsch; Peter Schindler, Bad Soden; Andreas Herling, Bad Camberg, all of Germany

[73] Assignee: Hoechst Aktiengesellschaft, Frankfurt am Main, Germany

[21] Appl. No.: 116,563

[22] Filed: Sep. 7, 1993

[30] Foreign Application Priority Data

Sep. 9, 1992 [DE] Germany .................. 42 30 067.3

[51] Int. Cl.$^6$ .................. C07D 25/04; C07D 401/08; C07D 403/08; A61K 31/47; A61K 31/415; A61K 31/41
[52] U.S. Cl. .................. 546/168; 518/253; 518/494; 518/304.7; 518/308.71; 560/115; 560/24
[58] Field of Search .................. 546/168; 548/308.7, 548/253, 494, 304.7, 308.7, 311.1; 514/253, 381, 382, 476, 414, 415, 532; 560/115, 24

OTHER PUBLICATIONS

E. Haslam et al., "the Shikimate Pathway. Part II. Conformational Analysis of (−)–Quinic Acid and Its Derivatives by Proton Magnetic Resonance Spectroscopy," J. Chem. Soc., pp. 1496–1500 (1971).
J. Soodsma et al., "The Inhibition by Phlorizin of Kidney Microsomal Inorganic Pyrophosphate–Glucose Phosphotransferase and Glucose 6–Phosphatase," J. Biol. Chem. 242, pp. 1955–1960 (1967).
B. Wallin et al., "The Requirement for Membrane Integrity in the Inhibition of Hepatic Glucose 6–Phosphatase by Sulfhydryl Reagents and Taurocholate," Biochem. Biophys. Res. Commun. 48, pp. 694–699 (1972).
M. Zoccoli et al., "Effect of Two Inhibitors of Anion Transport on the Hydrolysis of Glucose 6–Phosphate by Rat Liver Microsomes," J. Biol. Chem. 255, pp. 1113–1119 (1980).

*Primary Examiner*—David B. Springer
*Attorney, Agent, or Firm*—Finnegan, Henderson, Farabow, Garrett & Dunner

[57] ABSTRACT

Cyclohexane derivatives of the formula I

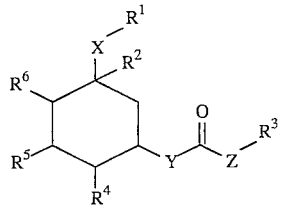

in which the radicals $R^1$ to $R^6$, X, Y and Z have the stated meanings, and processes for the preparation of these compounds are described. The compounds have valuable pharmacological properties and can therefore be used as pharmaceuticals.

11 Claims, No Drawings

SUBSTITUTED CYCLOHEXANE DERIVATIVES, PROCESSES FOR THEIR PREPARATION AND THE USE OF THE COMPOUNDS FOR TREATING DISEASES

The diabetes syndrome is characterized by elevated blood glucose levels. In insulin-dependent or type I diabetes, the cause is the death of the insulin-producing β cells of the pancreas; treatment is therefore by administration of insulin (replacement therapy). On the other hand, non- insulin-dependent or type II diabetes is characterized by a diminished effect of insulin on muscular and adipose tissue (insulin resistance) and an increased glucose production in the liver. The causes of these metabolic disturbances are still substantially unknown. The established therapy with sulfonylureas attempts to compensate for the insulin resistance by increasing endogenous insulin release but does not lead to normalization of the blood glucose level in all cases and is unable to prevent the disease progressing; many type II diabetics eventually become insulin-dependent, owing to "exhaustion" of the β cells, and suffer from late effects such as cataracts, nephropathies and angiopathies.

New therapeutic principles for the treatment of type II diabetes are therefore desirable.

The blood glucose concentration in the fasting state is determined by glucose production in the liver. Various research groups have been able to show that the elevation of blood glucose levels in type II diabetes correlates with a proportionate increase in glucose released by the liver. The glucose released into the blood by the liver can be formed both by breakdown of liver glycogen (glycogenolysis) and by gluconeogenesis. Glucose 6-phosphate is the common final product both of gluconeogenesis and of glycogenolysis. The terminal step in the hepatic liberation of glucose from glucose 6-phosphate is catalyzed by glucose-6-phosphatase (EC 3.1.3.9). Glucose-6-phosphatase is a multienzyme complex which occurs in the endoplasmic reticulum (ER). This enzyme complex is composed of a glucose-6-phosphate translocase which is present in the ER membrane, of a glucose-6-phosphatase which is localized on the luminal side of the endoplasmic reticulum, and of a phosphate translocase [for a review, see: Ashmore, J. and Weber G., "The Role of Hepatic Glucose-6-phosphatase in the Regulation of Carbohydrate Metabolism", in Vitamins and Hormones, Vol. XVII (Harris R. S., Marrian G. F., Thimann K. V., Eds), 92–132 (1959); Burchell A., Waddell I. D., "The molecular basis of the hepatic microsomal glucose-6-phosphatase system", Biochim. Biophys. Acta 1092, 129–137, (1990)]. The available wide-ranging literature shows that under all the investigated conditions which lead to elevated blood glucose levels in animal experiments, for example streptozotocin, alloxan, cortisone, thyroid hormones and starvation, the activity of this multienzyme complex is likewise increased. In addition, many investigations indicate that the increased glucose production observed in type II diabetics is associated with an increased glucose-6-phosphatase activity. The importance of the glucose-6-phosphatase system for normal glucose homeostasis is further underlined by the hypoglycemic symptoms of patients with type Ib glycogenosis who lack the translocase component of the glucose-6-phosphatase system.

A reduction in glucose-6-phosphatase activity by suitable active substances (inhibitors) ought to lead to a corresponding reduction in hepatic liberation of glucose. These active substances ought to be able to suit hepatic glucose production to the effective peripheral consumption. The resulting reduction in blood glucose levels in the fasting state of type II diabetics ought in addition to have a preventive effect in respect of the late effects of diabetes. A number of non-specific inhibitors of glucose-6-phosphatase have been described in the literature, such as, for example, phlorrhizin [Soodsma, J. F., Legler, B. and Nordlie, R. C., J. Biol. Chem. 242, 1955–1960, (1967)], 5,5'-dithiobis-2-nitrobenzoic acid [Wallin, B. K. and Arion, W. J., Biochem. Biophys. Res. Commun. 48, 694–699, (1972)], 2,2'-diisothiocyanatostilbene and 2-isothiocyanato-2'-acetoxystilbene [Zoccoli, M. A. and Karnowski, M. L., J. Biol. Chem. 255, 1113–1119, (1980)]. However, to date no therapeutically utilizable inhibitors of the glucose-6-phosphatase system are yet available.

The cyclohexane derivatives which are characterized in detail hereinafter are novel compounds which have not to date been described in the chemical and biological literature. We have now found that certain esters of substituted cyclohexanecarboxylic acids, such as, for example, Example 14, are inhibitors of the glucose-6phosphatase system.

The invention therefore relates to cyclohexane derivatives of the formula I

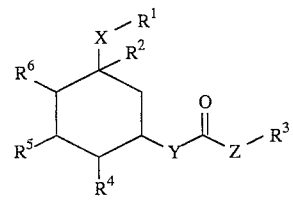

in which the radicals have the following meanings:

$R^1$: CN, COOH, a COOH group protected by a protective group, $C_1$–$C_4$-alkanoyl, $SO_3$—$C_1$–$C_4$-alkyl, $SO_3H$, $SO_2NR^8R^9$, $PO(OH)_2$, $PO(OH)(O$—$C_1$–$C_4$-alkyl), $PO(O$—$C_1$–$C_4$-alkyl)_2$, $R^2$: $C_1$–$C_{10}$-alkyl $(R^{11})_n$, O—$C_1$–$C_{10}$-alkyl $(R^{11})_n$, $C_2$–$C_{10}$-alkenyl $(R^{11})_n$, O—$C_3$–$C_{10}$-alkenyl $(R^{11})_n$, $C_2$–$C_{10}$-alkynyl $(R^{11})_n$, O—$C_3$–$C_{10}$-alkynyl $(R^{11})_n$, S—$C_1$–$C_{10}$-alkyl $(R^{11})_n$, S—$C_3$–$C_{10}$-alkenyl $(R^{11})_n$, S—$C_3$–$C_{10}$-alkynyl $(R^{11})_n$, NH—$C_1$–$C_{10}$-alkyl $(R^{11})_n$, NH—$C_3$–$C_{10}$-alkenyl $(R^{11})_n$ or NH—$C_3$–$C_{10}$-alkynyl $(R^{11})_n$, where $R^{11}$ is optionally substituted in each case by $R^{12}$;

$R^3$, $R^{11}$ and $R^{13}$: alkyl with 1 to 10 carbon atoms, cycloalkyl with 3–8 ring carbon atoms, phenyl, naphthyl, phenanthryl, pyridyl, thienyl, furyl, pyrimidyl, indolyl, imidazolyl, coumarinyl, phthaliminyl, quinolyl, piperazinyl, tetrazolyl, triazolyl, oxazolyl or their thieno-, pyridino-, pyrimidino- or benzo-fused derivatives, it being possible for the aromatic or heteroaromatic system to be substituted one or more times, identically or differently, by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl, and $R^3$, $R^{11}$ and $R^{13}$ are identical or different;

$R^4$, $R^5$ and $R^6$: H, OH an OH group which is protected by conventional alcohol-protective groups, F, Cl, Br or the meanings stated for $R^2$, where $R^4$, $R^5$ and $R^6$ are identical or different;

$R^7$: $C_1$–$C_4$-alkyl, phenyl or benzyl;

$R^8$ and $R^9$: H, $C_1$–$C_4$-alkyl, $C_1$–$C_4$-alkanoyl, phenyl which is optionally substituted by F, Cl, Br, I, OH, O—$C_1$–$C_4$-alkyl, $CF_3$, —$NO_2$ or CN, where $R^8$ and $R^9$ are identical or different, or $R^8$ and $R^9$ form together with the nitrogen atom a 4- to 10-membered, saturated heterocyclic ring in which a $CH_2$ group can optionally be replaced by O, S or $NR^{10}$, $R^{10}$: H, $C_1$-$C_4$-alkyl, phenyl or benzyl $R^{12}$: phenyl, naphthyl, phenanthryl, pyridyl, thienyl, furyl, pyrimidyl, indolyl, imidazolyl, coumarinyl, phthaliminyl, quinolyl, piperazinyl, tetrazolyl, triazolyl, oxazolyl or their thieno- or benzo-fused derivatives, it being possible for the aromatic or heteroaromatic system to be substituted one or more times, identically or differently, by F, Cl, Br, I, OH, $CF_3$, $-NO_2$, CN, $C_1$-$C_4$-alkoxy, $C_1$-$C_4$-alkyl, $C_2$-$C_4$-alkenyl, $NR^8R^9$, phenyl, benzyl, thienyl, furyl, imidazolyl, pyridyl, O-phenyl or O-benzyl;

X: $(CH_2)_m$, $-CH=CH-$, $-C\equiv C-$, $-CH_2-O-CH_2-$, $-CH_2-S-CH_2-$ or $-CH_2-N-CH_2-$,
        $|$
        $R^8$ Y: $(CH_2)_m$, O, S, $NR^8$, Z: $(CH_2)_m$, S, O, S—$C_1$-$C_{10}$-alkyl, O— $C_1$-$C_{10}$-alkyl, CH=CH, CH=CF, CH=CCl, CH=CBr, $CH_2$—CO, $CH_2$—CHF, $CH_2$—CHCl, $CH_2$—CHBr, $CH_2$—CHI, $C_3$-$C_{10}$-cycloalkylene, $C_3$-$C_{10}$-cycloalkenylene, it being possible for 1 to 3 ring carbon atoms to be replaced by sulfur, oxygen or nitrogen atoms, $COOR^7$, C≡C, CH=C($C_1$-$C_4$-alkyl), CH=C(CN), CH=C($NR^8R^9$), CH=C($C_1$-$C_4$-alkanoyl), CH=C($R^{13}$), $NR^8$ and when Y is oxygen, $-C-Z-R^3$
$\|$
$O$ can together be an amino-acid residue selected from the group comprising Ala, Arg, Asn, Asp, Cys, Gln, Glu, Gly, His, Ile, Leu, Lys, Phe, Pro, Ser, Thr, Trp, Tyr and their derivatives protected by conventional protective groups, n: zero, 1 or 2 m: zero, 1, 2, 3 or 4.

The compounds of the formula I according to the invention can, if they contain a carboxyl group, form salts with inorganic or organic bases. The invention therefore also relates to the physiologically tolerated salts of compounds of the formula I.

The compounds of the formula I according to the invention contain a number of stereo centers. The invention relates to all possible enantio- and diastereomers. They are all represented by the formula I. Unless otherwise indicated, the following applies to the statements hereinbefore and hereinafter: the alkyl, alkanoyl and alkoxy radicals indicated for $R^1$, $R^3$, $R^7$, $R^8$, $R^9$, $R^{11}$, $R^{12}$, $R^{13}$ and Z are straight-chain or branched. The alkyl, alkenyl and alkynyl groups indicated for $R^2$ and $R^{12}$ are straight-chain, branched or cyclic, it also being possible for only a part of the radical to form a ring.

One of the $CH_2$ groups can be replaced by O, S, $SO_2$ or $NR^8$, $R^{11}$ can be substituted by $R^{12}$ and, when n=2, the two $R^{11}$ radicals are identical or different. Unsaturated radicals are unsaturated one or more times.

A COOH radical which is protected by a protective group means COO—$C_1$-$C_{10}$-alkyl (unbranched or branched or cyclic), COO—CH($R^7$)—O—$C_1$-$C_4$-alkanoyl (unbranched or branched), COO-benzyl, COO-phenyl, $CONH_2$, CONH-$C_1$-$C_{10}$-alkyl (unbranched and branched), —$CONR^8R^9$ where $R^7$, $R^8$ and $R^9$ have the stated meanings.

Alcohol-protective groups are:

Substituted ethers such as methoxymethyl, methylthiomethyl, t-butylthiomethyl, benzyloxymethyl, p-methoxybenzyloxymethyl, t-butoxymethyl, siloxymethyl, 2-methoxyethoxymethyl, 1-ethoxyethyl, allyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl.

Protective groups for amino acids are:

a) Carbamates such as methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10, 10,10-tetrahydrothioxanthyl)]methyl, 4-methoxyphenacyl, 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkylthio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl, t-amyl, S-benzyl-thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di-(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6- tri-t-butylphenyl, 4-(trimethylammonium)benzyl and 2,4,6-trimethylbenzyl.

b) Urea derivatives such as 10-phenothiazinylcarbonyl derivatives, N'-p-toluenesulfonylaminocarbonyl and N'-phenylaminothiocarbonyl.

c) Amides such as N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivatives, N-benzoyl and N-p-phenylbenzoyl.

Preferred compounds of the formula I are those in which $R^1$ is CN, COOH, a COOH group which is protected by a protective group, or $C_1$-$C_4$-alkanoyl, and the other radicals have the abovementioned meanings. Particularly preferred compounds of the formula I are those in which the radicals have the following meanings:

$R^1$: CN, COOH, a COOH group which is protected by a protective group, or $C_1$-$C_4$-alkanoyl $R^2$: O—$C_1$-$C_{10}$-alkyl($R^{11}$)$_n$ (n=0,1,2), where the alkyl moiety is unbranched or branched or cyclic, and one of the $CH_2$ groups can be replaced by O, and $R^{11}$ can be substituted by $R^{12}$ and when n=2 the two $R^{11}$ radicals are identical or different. O—$C_3$-$C_{10}$-alkenyl($R^{11}$)$_n$ (n=0,1,2), where the alkenyl moiety is unbranched, branched or cyclic, one of the $CH_2$ groups can be replaced by O, S, SO, $SO_2$ or $NR^8$, and is unsaturated one or more times, and $R^{11}$ can be substituted by $R^{12}$, and when n=2 the two $R^{11}$ radicals are identical or different, O—$C_3$–$C_{10}$-alkynyl($R^{11})_n$ (n=0,1,2), where the alkynyl moiety is unbranched, branched or cyclic and is unsaturated one or more times, and one of the $CH_2$ groups can be replaced by O, S, SO, $SO_2$ or $NR^8$, and $R^{11}$ can be substituted by $R^{12}$ and when n=2 the two $R^{11}$ radicals are identical or different, $R^3$ to $R^{13}$ have the abovementioned meanings, X: $(CH_2)_m$ (m=0,1,2,3,4), CH=CH, C≡C, $CH_2OCH_2$, $CH_2SCH_2$ Y: $(CH_2)_m$ (m=0,1,2,3,4), O, S, $NR^8$, Z: $(CH_2)_m$ (m=0,1,2,3,4), S, O, S—$C_1$–$C_{10}$-alkyl, (unbranched or branched), CH=CH, CH=CF, CH=CCl, CH=CBr, $CH_2$—C(O), $CH_2$—CHF, $CH_2$—CHCl, $CH_2$—CHBr, $CH_2$—CHI, $C_3$–$C_{10}$-cycloalkylene, $C_3$–$C_{10}$-cycloalkenylene, $COOR^7$, C≡C, CH=C($C_1$–$C_4$-alkyl) (unbranched or branched), CH=C(CN), CH=C($R^{13}$), $NR^8$.

The compounds of the formula I according to the invention can, if they contain a carboxyl group, form salts with inorganic or organic bases. Preferred salts are those with inorganic bases, especially the physiologically acceptable alkali metal salts, in particular sodium and potassium salts.

The compounds of the formula I inhibit the glucose-6-phosphatase system of the liver in mammals. The compounds are therefore suitable as pharmaceuticals. The invention therefore also relates to pharmaceuticals based on the compounds of the formula, where appropriate in the form of the physiologically tolerated salts.

The invention furthermore relates to the use of compounds of the formula I or the salts for the treatment of diseases associated with an increased activity of the glucose-6-phosphatase system.

The invention also relates to the use of compounds of the formula I or the salts for the treatment of diseases associated with an increased hepatic glucose production.

The invention additionally relates to the use of compounds of the formula I or the salts for the treatment of type II diabetes (non-insulin-dependent or adult-onset diabetes).

The invention additionally comprises the use of compounds of the formula I or the salts for the production of pharmaceuticals for the treatment of diabetes and other disorders characterized by an increased output of glucose from the liver or an increased activity of the glucose-6-phosphatase system.

The effect of the compounds according to the invention on the glucose-6-phosphatase system has been investigated in an enzyme assay in liver microsomes.

To prepare the microsomal fraction containing the glucose-6-phosphatase, fresh liver organs from male Wistar rats were used and processed as described in the literature [Canfield, W. K. and Arion, W. J., J. Biol. Chem. 263, 7458–7460, (1988)]. This microsomal fraction can be stored at −70° C. without significant loss of activity for at least 2 months. The glucose-6-phosphatase activity was detected as indicated in the literature [Arion, W. J. in Methods Enzymol. 174, Academic Press 1989, pages 58–67] by determining the phosphate liberated from glucose-6-phosphate. 0.1 ml of assay mixture contained glucose-6-phosphate (1 mmol/l), the test substance, 0.1 mg of microsomal fraction and 100 mmol/l HEPES buffer (4-(2-hydroxyethyl)piperazine-1-ethanesulfonic acid), pH 7.0. The reaction was started by adding the enzyme. After 20 min at room temperature, the reaction was stopped by adding 0.2 ml of phosphate reagent. The sample was incubated at 37° C. for 30 min, and the absorption (A) of the blue color was subsequently measured at 570 nm. The inhibitory activity of the test substance was found by comparison with a control reaction which contained no test substance, using the formula $$\text{percent inhibition} = \frac{A(\text{control}) - A(\text{test substance})}{A(\text{control})} \times 100$$

Where necessary, the inhibitory effect of the test substance was determined as a function of the test substance concentration employed, and from this the concentration for 50% inhibition of enzyme activity ($IC_{50}$) was calculated.

The $IC_{50}$ was determined for the compounds listed hereinafter:

Example 1

[1S,3R,4R,5S]-3-[(E)-3-(4-hydroxyphenyl)propenoyl]oxy-4,5-dihydroxy-1-phenylmethyloxy-cyclohexanecarboxylic acid $IC_{50}$=190 μM Example 2

[1S,3R,4R,5S]-3-[(E)-3-(4-hydroxyphenyl)propenoyl]oxy-4,5-dihydroxy-1-(2-thienylmethyl)oxy-cyclohexanecarboxylic acid $IC_{50}$=110 μM Example 3

[1S,3R,4R,5S]-3-[(E) -3-(4-hydroxyphenyl)propenoyl]oxy-4,5-dihydroxy-1-(2-propynyl)oxy-cyclohexanecarboxylic acid $IC_{50}$=560 μM Example 8

[1S,3R,4R,5S]-3-[(E)-3-(4-hydroxyphenyl)propenoyl]oxy-4,5-dihydroxy-1-propyloxy-cyclohexanecarboxylic acid $IC_{50}$=230 82 M Example 4

[1S,3R,4R,5S]-1-(4-chlorophenylpropyl)oxy-4,5-dihydroxy-3-(2-pyridinecarbonyl)oxy-cyclohexanecarboxylic acid $IC_{50}$=26 μM Example 44

[1S,3R,4R,5S]-1-(4-chlorophenylpropyl)oxy-3-[(E)-3-(4-hydroxyphenyl)propoyl]oxy-4,5-dihydroxy-cyclohexanecarboxylic acid $IC_{50}$=9.3 μM

TABLE

| Compound from Example | $IC_{50}$ [μM] |
|---|---|
| 69 | 170 |
| 113 | 3.7 |
| 114 | 5.0 |

TABLE-continued

| Compound from Example | $IC_{50}$ [μM] |
| --- | --- |
| 115 | 8.9 |
| 116 | 4.5 |
| 117 | 41.0 |
| 118 | 1.3 |
| 119 | 12.0 |
| 120 | 0.69 |

The compounds of the formula I according to the invention in which the radicals $R^2$-O-alkyl$(R^{11})_n$, O-alkenyl$(R^{11})_n$, or O-alkynyl$(R^{11})_n$, $R^4=R^5=$OH and Y=O can be prepared by route A indicated in the following diagram.

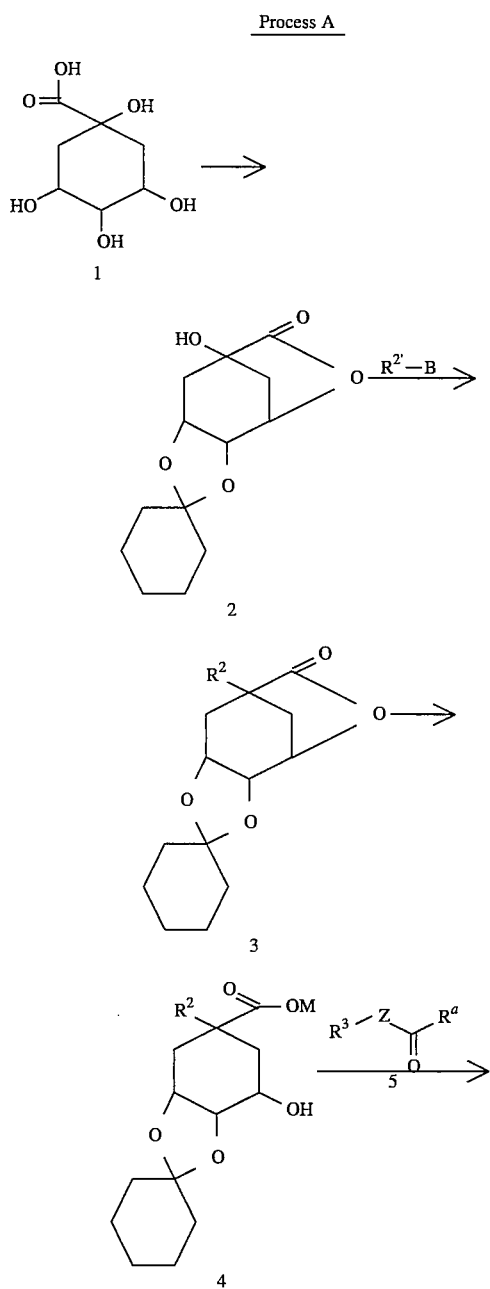

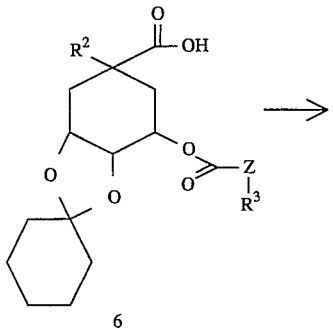

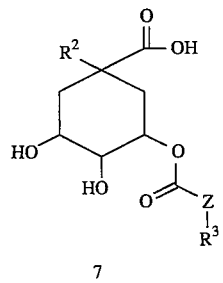

M: alkali metal $R^a$: Cl, Br,

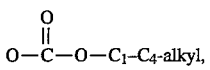

imidazolyl, triazolyl or tetrazolyl

B: chlorine, bromine, iodine, sulfonic ester $R^{2'}$: alkyl$(R^{11})_n$, alkenyl$(R^{11})_n$ or alkynyl$(R^{11})_n$ (7=formula I, $R^2$=O—$C_1$-$C_{10}$-alkyl$(R^{11})_n$, O—$C_3$-$C_{10}$-alkenyl$(R^{11})_n$ or O—$C_3$-$C_{10}$-alkynyl $(R^{11})_n$, $R^4=R^5=$OH, $R^6$=H, Y=O, X=$(CH_2)_m$ with m=zero, $R^1$=COOH, Z, $R^3$, $R^{11}$ and n as indicated for formula I).

Process A comprises compound 2, which is known from the literature and can be obtained from compound 1, being deprotonated with a strong base such as potassium tert-butylate, sodium hydride or potassium hydride and, to introduce $R^2$, reacted with appropriate halides, trifluorosulfonic esters, methylsulfonic esters or p-toluenesulfonic esters, advantageously in polar aprotic solvents such as dimethylformamide, dimethyl sulfoxide or tetrahydrofuran, resulting in compound 3. Preferably used as base is sodium hydride and as solvent is dimethylformamide.

The reaction of 2 to give 3 is carried out at temperatures from −20° C. to the boiling point of the solvent used. A temperature range from −10° to 60° C., especially from 0° to 30° C., is preferred The preferred embodiment of the reaction of 2 to give 3 is carried out in dimethylformamide in the presence of sodium hydride or potassium hydride at temperatures from 0° to 60° C. The reaction is moreover advantageously carried out with exclusion of moisture under a protective gas (nitrogen or argon).

The starting materials which are needed for the conversion of 2 into 3 and which correspond to the radical $R^2$ can be prepared by standard processes known to the skilled worker. These take the form of structures of the type $R^2$-B with the restriction mentioned for process A (although without the linking oxygen atom). B is, for example, a leaving group such as Cl, Br, I or $OSO_2R$ ($R=CH_3$, Ph, tolyl, $CF_3$).

In place of the cyclohexylidene protective group in 2 or 3, it is also possible to use other protective groups which can be eliminated under mild acidic conditions such as isopropylidene acetals or benzylidene acetals as well as tert-butyl, methoxymethyl, 1-ethoxyethyl or tetrahydropyranyl ethers, silyl ethers such as trimethylsilyl or tert-butyldimethylsilyl or carbonates such as benzyloxycarbonyl and tert-butoxycarbonyl derivatives which are well known from peptide and steroid chemistry. Compound i is likewise the starting material for the preparation of such protected compounds.

A further step in process A is the hydrolysis of the lactone 3 to the alkali metal salt 4 with alkali metal hydroxides such as lithiumhydroxide, sodiumhydroxide or potassium hydroxide. The reaction is advantageously carried out in protic or aprotic solvents such as lower alcohols, tetrahydrofuran or dioxane, and the use of dioxane is preferred.

The reaction of 3 to give 4 is carried out at temperatures from $-20°$ C. to the boiling point of the solvent used. A temperature range from $-10°$ to $60°$ C., in particular from $0°$ to $30°$ C. is preferred.

A further step is the reaction of 4 to give 6 in which the radical $R^3$—Z—C(O)— is attached to 4. To do this, 4 is reacted in an aprotic organic solvent such as, for example, tetrahydrofuran, dimethylformamide, dichloromethane, pyridine or dimethyl sulfoxide with a compound $R^3$—Z—C(O)—$R^a$ (5) where $R^a$ can be, for example, Cl, Br, OC(O)—$C_1$-$C_4$-alkyl, imidazolyl, triazolyl or tetrazolyl, with imidazolyl and triazolyl being particularly preferred. The reaction is particularly preferably carried out in dimethylformamide in the presence of a base such as, for example, sodium hydride, potassium hydride, 4-dialkylaminopyridine or tert-amines, but especially of sodium hydride.

The reaction of 4 to give 6 is carried out at temperatures from $-20°$ C. to the boiling point of the solvent used. A temperature range from $-10°$ to $60°$ C., particularly from $0°$ to $30°$ C., is preferred.

The compounds $R^3$—Z—C(O)—$R^a$ (5) can be prepared by standard processes known to the skilled worker.

A preferred embodiment of the reaction of 4 to give 6 comprises the reaction of 4 with sodium hydride in dimethylformamide and subsequent addition of a solution of $R^3$—Z—C(O)-imidazole (5) in dimethylformamide at 0 to $20°$ C., advantageously with exclusion of moisture under protective gas (argon or nitrogen).

The elimination of the protective group in the reaction of 6 to give 7 is carried out in a generally known manner, for example by treatment with dilute inorganic acids such as, for example, hydrochloric acid or strong organic acids such as, for example, trifluoroacetic acid in inert organic solvents such as cyclic ethers, optionally in the presence of water, at temperatures from $-20°$ C. to the boiling point of the solvent, preferably from $0°$ to $30°$ C.

The resulting compounds of the formula I according to the invention can, if they contain a carboxyl group, form salts with inorganic or organic bases. Also preferred therefore are such salts with inorganic bases, especially the physiologically acceptable alkali metal salts, in particular sodium and potassium salts.

The esters indicated for $R^1$ can be prepared from the alkali metal salts of the compounds of the formula I with a carboxyl group. To do this, compound 7 is reacted in an inert organic solvent such as tetrahydrofuran, dimethyl sulfoxide, preferably dimethylformamide, at $-10°$ to $60°$ C., for example with a $C_1$-$C_4$-alkyl halide, preferably $C_1$-$C_4$-alkyl iodide, benzyl bromide or $C_1$-$C_4$-alkanoyl-O—CH($R^7$)-Br or $C_1$-$C_4$-alkanoyl-O—CH($R^7$)—I to give the compounds of the formula I according to the invention with an ester group as $R^1$ and X=$(CH_2)_m$ m=0 with the details mentioned for process A.

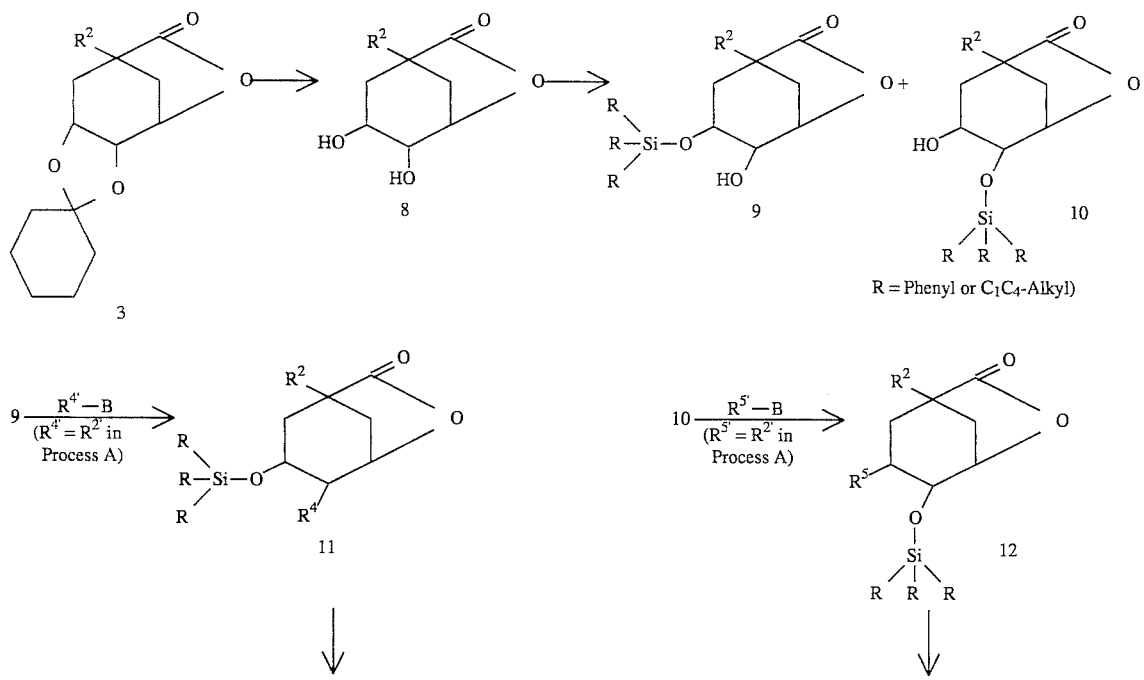

Process B (see process A for definition of M, $R^a$ and B)

-continued
Process B (see process A for definition of M, $R^a$ and B)

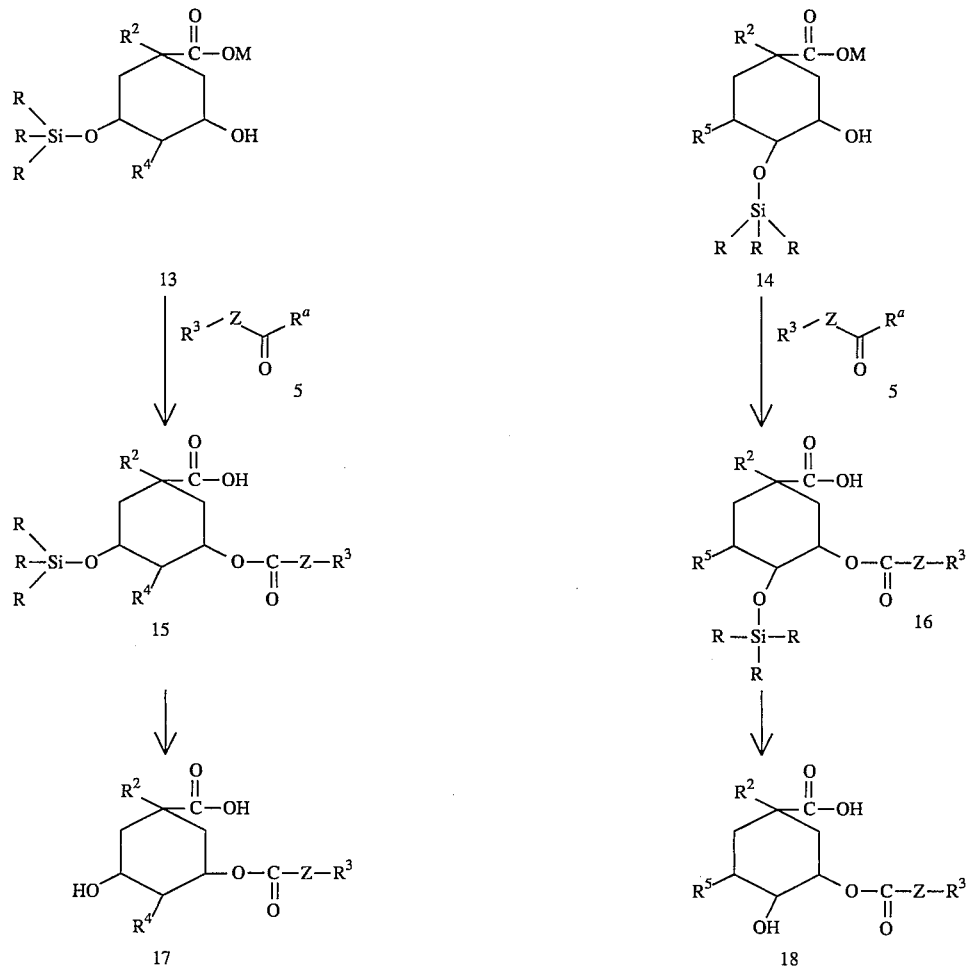

(17 and 18=formula I with $R^2$=O—$C_1$–$C_{10}$-alkyl($R^{11}$)$_n$, O—$C_3$–$C_{10}$-alkenyl($R^{11}$)$_n$ or O—$C_3$–$C_{10}$-alkynyl($R^{11}$)$_n$, $R^4$ in the meaning indicated for $R^2$ and $R^5$=OH or $R^4$=OH and $R^5$ in the meaning indicated for $R^2$, $R^6$=H, Y=O, X=$(CH_2)_m$ with m=zero, $R^1$=COOH, Z, $R^3$ and $R^{11}$ and n as indicated for formula I).

Process B is used in order to vary the radicals $R^4$ and $R^5$. In this case it is necessary to eliminate the cyclohexylidene protective group in 3 to give the compound 8. This can take place by a standard process known to the skilled worker. Preferred in this case is hydrolysis of in inert organic solvents such as lower alcohols in the presence of strong organic acids such as sulfonic acids, for example p-toluenesulfonic acid or trifluoroacetic acid.

The reaction of 3 to give 8 is carried out, for example, at temperatures from −20° C. to the boiling point of the solvent used. A temperature range from −10° to +60° C., in particular from 20° to 50° C., is preferred. The conversion of 3 into 8 is particularly preferably carried out in isopropanol in the presence of p-toluenesulfonic acid at 40° C.

A step characteristic of process B is the differentiation of the two free hydroxyl groups in 8. To do this, compound 8 is reacted with sterically demanding trialkylsilyl halides such as, for example, tert-butyldimethylsilyl chloride, tert-butyldiphenylsilyl chloride or triisopropylsilyl chloride in an inert organic solvent, in particular dimethylformamide, at temperatures between −10° and 40° C. in the presence of a base, in particular imidazole, to give the compounds 9 and 10 which can be separated by chromatography.

The compounds 9 and 10 can be reacted in analogy to the conversions of 2 into 7 from process A so that the variations for the radicals $R^4$ and $R^5$ indicated for formula I are possible by this process.

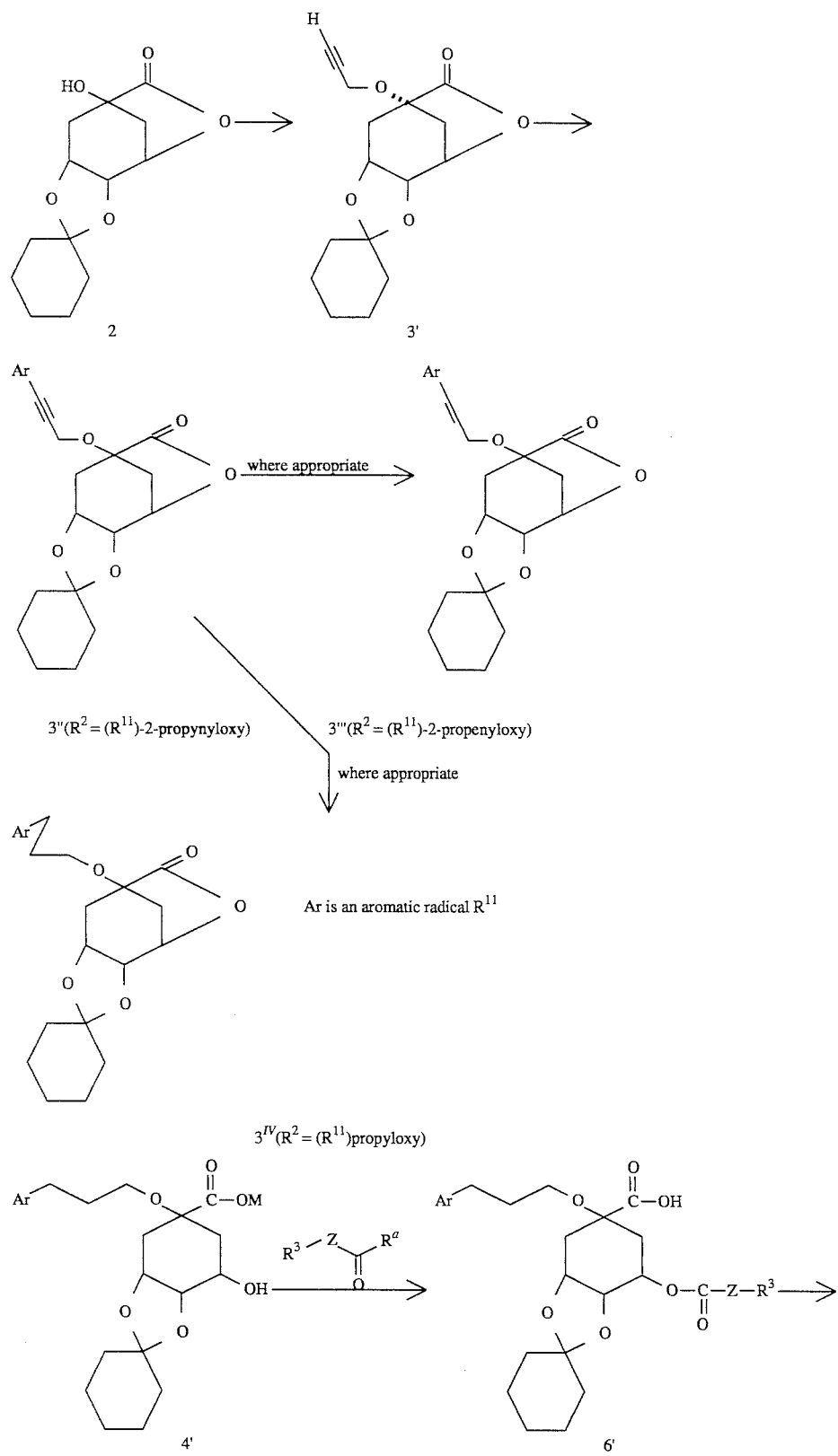
Process C (see process A for definition of $R^a$)

-continued
Process C (see process A for definition of $R^a$)

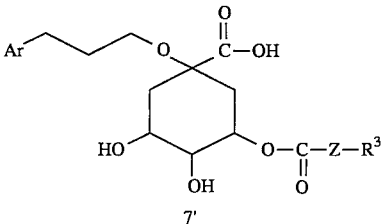

7'

(7'=formula I with $R^2$=O—$C_3$-alkyl($R^{11}$)$_n$ with n=1 and $R^{11}$ aromatic radical as indicated for formula I, $R^4$, $R^5$=OH, $R^6$=H, Y=O, X=(CH$_2$)$_m$ with m=zero and $R^1$=COOH, Z and $R^3$ as indicated for formula I, with compounds with $R^2$=O—$C_3$-alkenyl($R^{11}$)$_n$ or O—$C_3$-alkynyl($R^{11}$)$_n$ being obtained when the optional hydrogenation to 3''' or $3^{IV}$ is omitted).

An alternative process to A for a number of compounds of the formula I according to the invention is process C. The intermediate 3' in which $R^2$=2-propynyloxy can be used for $R^2$=O—$C_3$-alkynyl($R^{11}$). In this case, 3'($R^2$= 2-propynyloxy) is reacted in an inert organic solvent such as, for example, toluene, benzene or n-heptane with catalysis by a palladium complex and copper(I) halide, especially copper(I) iodide, with an aryl halide, especially aryl bromide or aryl iodide, to give 3'' ($R^2$=$R^{11}$-2-propynyloxy). To do this it is necessary to add a base such as, for example, primary, secondary or tertiary amines, especially triethylamine. It is also optionally possible for the base simultaneously to act as solvent and for addition of another organic solvent to be dispensed with.

The reaction of 3' ($R^2$=2-propynyloxy) to give 3'' ($R^2$= $R^{11}$-2-propynyloxy) is carried out at temperatures from –20° C. to the boiling point of the solvent used. A temperature range from 20° to 90° C., in particular from 60° to 80° C., is preferred The palladium complex which can be used is, for example, the ditriphenylphosphinepalladium dichloride complex which can be prepared in situ from palladium dichloride and triphenylphosphine, or the ditriphenylphosphinepalladium diacetate complex which can be obtained in the same way from palladium(II) acetate, and ditriphenylphosphinepalladiumdichloride is preferred.

3''' ($R^2$=$R^{11}$-2-propenyloxy) or $3^{IV}$ ($R^2$=$R^{11}$-2-propyloxy) can be prepared from 3'' ($R^2$=$R^{11}$-2-propynyloxy) using hydrogenation catalysts. The reactions are carried out in ethanol or pyridine under a hydrogen atmosphere at atmospheric pressure.

The reaction of 3'' ($R^2$=$R^{11}$-2-propynyloxy) to give 3''' ($R^2$=$R^{11}$-2-propenyloxy) is carried out with a palladium on barium sulfate catalyst at temperatures from 0° C. to the boiling point of the solvent used. Pyridine is preferred as solvent at a temperature range from 20° to 50° C., in particular from 20° to 30° C.

The reaction of 3''' ($R^2$=$R^{11}$-2-propynyloxy) to give $3^{IV}$ ($R^2$=($R^{11}$)propyloxy) is carried out with palladium on charcoal as catalyst in ethanol at temperatures from –20° C. to the boiling point of the solvent used. A temperature range from 20° to 50° C., in particular from 20° to 30° C., is preferred.

The further reactions of $3^{II-IV}$ and of 4' to give 7', i.e. to give the compounds of the formula I, are described in detail under process A.

Process D (see process A for definition of $R^a$)

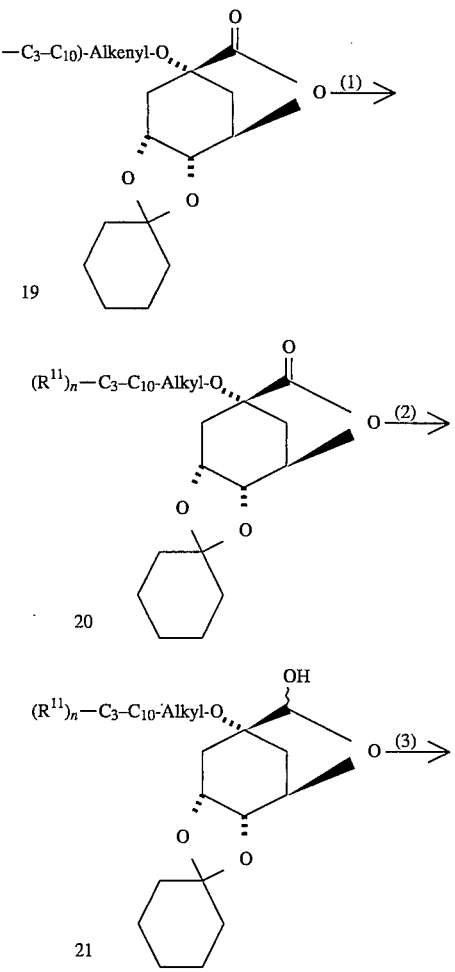

-continued
Process D (see process A for definition of $R^a$)

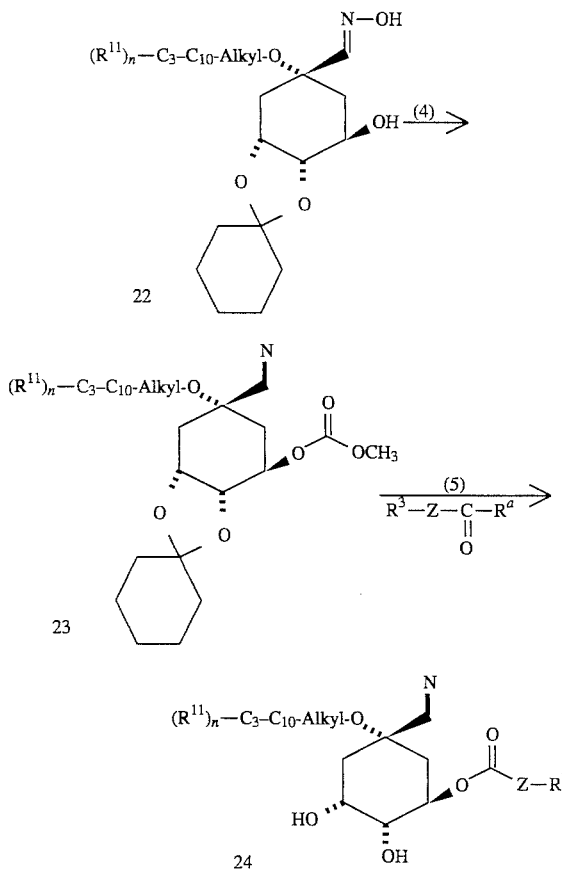

(24=formula I with $R^1$=CN, X=(CH$_2$)$_m$ with m=zero, $R^2$=O—C$_3$–C$_{10}$-alkyl-(R$^{11}$)$_n$, with n=zero or 1, $R^4$, $R^5$=OH, $R^6$=H, Y=O and $R^3$, $R^{11}$ and Z as indicated for formula I).

The procedure for process D corresponding to process steps (1) to (5) is explained in Example 68.

Process E (see process A for definition of $R^a$)

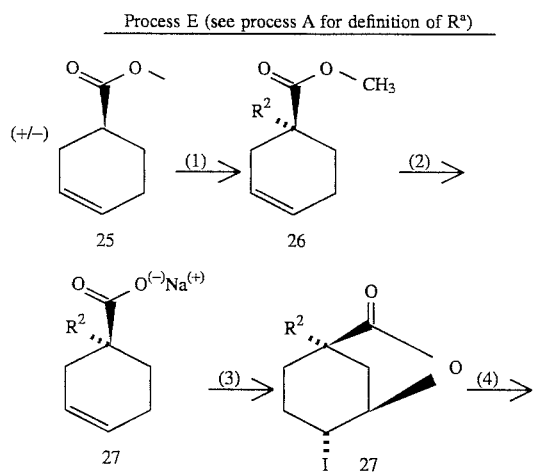

-continued
Process E (see process A for definition of $R^a$)

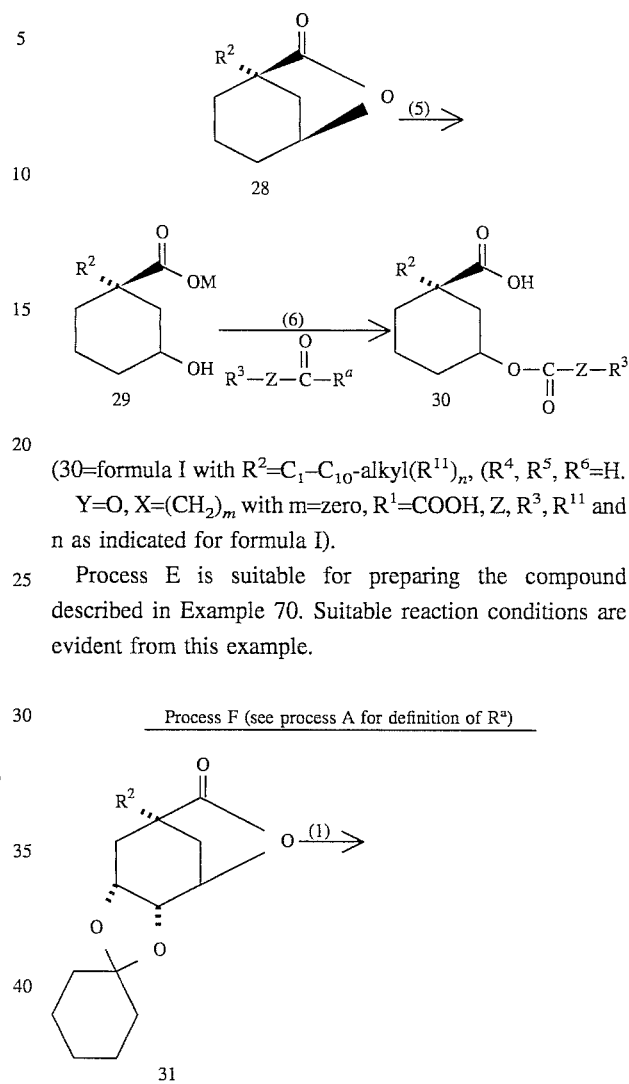

(30=formula I with $R^2$=C$_1$–C$_{10}$-alkyl(R$^{11}$)$_n$, ($R^4$, $R^5$, $R^6$=H, Y=O, X=(CH$_2$)$_m$ with m=zero, $R^1$=COOH, Z, $R^3$, $R^{11}$ and n as indicated for formula I).

Process E is suitable for preparing the compound described in Example 70. Suitable reaction conditions are evident from this example.

Process F (see process A for definition of $R^a$)

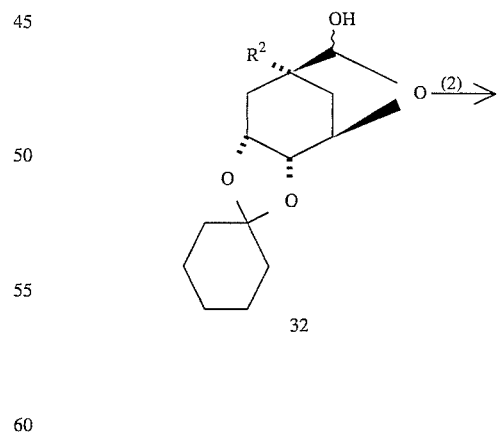

-continued
Process F (see process A for definition of $R^a$)

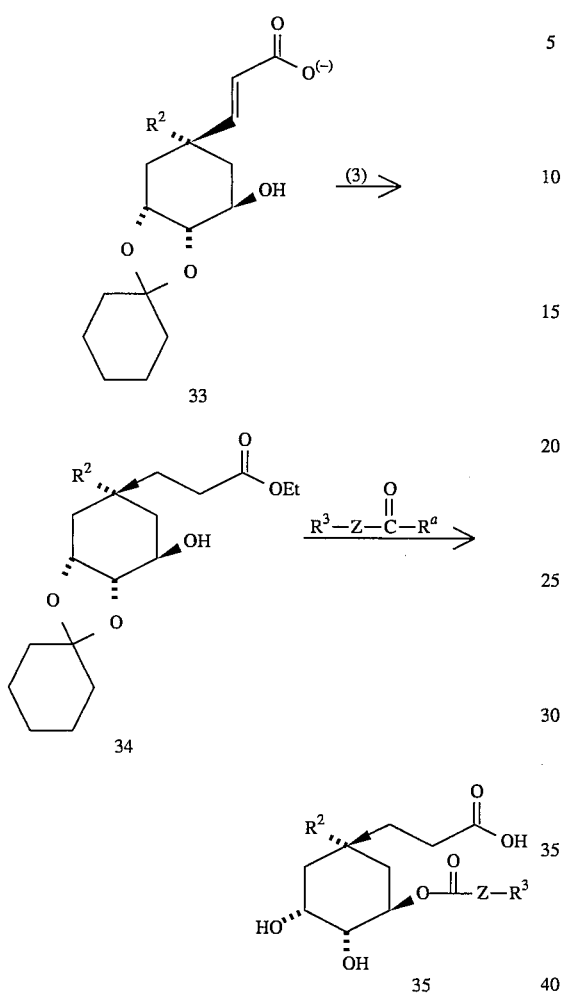

(35=formula I with $R^1$=COOH, X=$(CH_2)_m$ with m=3, $R^2$=O—$C_1$–$C_{10}$-alkyl($R^{11}$)$_n$, O—$C_3$–$C_{10}$-alkenyl($R^{11}$)$_n$ or O—$C_3$–$C_{10}$-alkynyl($R^{11}$)$_n$, $R^4$, $R^5$=OH, $R^6$H and Z, $R^3$, $R^{11}$ and n as indicated for formula I).

The process is explained in Example 63.

The starting compounds for processes A to F are known or can be prepared in analogy to the methods known from the literature or can be obtained by the processes described in the application.

Compound 5 (compare process A) which is employed, for example, for synthesizing the compounds of Examples 68, 78, 82, 96, 97 and 98 is expediently prepared by process I, II, III as described hereinafter.

Process I

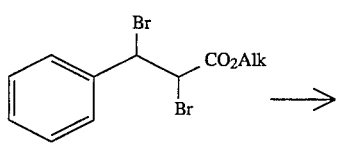

-continued

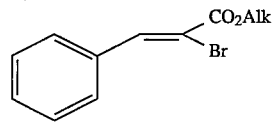

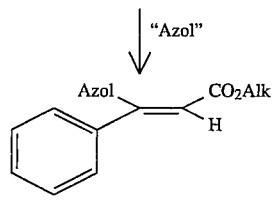

Process II

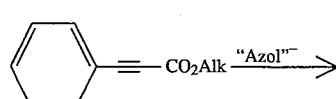

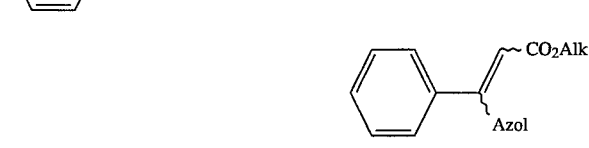

Process III

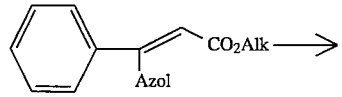

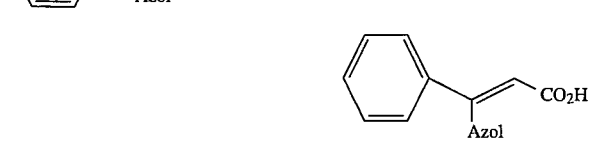

Alk is $C_1$–$C_4$-alkyl

Azol is $R^{13}$ meaning imidazolyl, indolyl, piperazinyl, tetrazolyl, triazolyl or their thieno-, pyridino-, pyrimidino- or benzo-fused derivatives.

Process I

Preparation of β-Azol-substituted methyl cinnamates

A mixture of 50 g of methyl 2,3-dibromo-3-phenylpropanoat, 100 ml of triethylamine and 500 ml of toluene is heated to boiling for 1 h and then cooled to room temperature and filtered. The filtrate is evaporated in vacuo, and the resulting α-bromocinnamic acid is used further without purification. 0.2 mol of the Azol derivative dissolved in 150 ml of anhydrous DMF is added dropwise to a stirred suspension of 4.7 g of NaB (80% in mineral oil) in 100 ml of anhydrous DMF. The temperature of the mixture is maintained below 35° C. during this by cooling in ice. After the addition is complete, the mixture is stirred at room temperature for 1 h. The previously prepared α-bromocinnamic acid is dissolved in 200 ml of anhydrous DMF and, while cooling in ice, the solution of the Azol sodium salt is added dropwise with stirring. After stirring at room temperature for 2 hours, 10.8 ml of glacial acetic acid are added, the mixture is stirred into 1.5 l of ice-water and extracted several times with ethyl acetate, and the organic phases are washed with water. The organic phases are dried and evaporated in vacuo, and the residue is purified by column chromatography on silica gel (mobile phase: n-heptane/ethyl acetate) or recrystallization.

Process II

Preparation of β-Azol-substituted ethyl cinnamates

A mixture of 20 g of ethyl phenylpropiolate, 0.11 mol of Azol derivative and 15 ml of anhydrous DMF is stirred while passing in argon at room temperature. A spatula of NaH (80% in mineral oil) is added. When evolution of hydrogen has ceased, the mixture is heated to 100°–150° C. (bath temperature) and the reaction is followed by TLC (mobile phase n-heptane/ethyl acetate). After the reaction is complete, the mixture is cooled to room temperature and concentrated in vacuo, and the residue is recrystallized from n-heptane or diluted with a little n-heptane/ethyl acetate and purified by column chromatography on silica gel (mobile phase: n-heptane/ethyl acetate).

Process III

Preparation of β-Azol-substituted cinnamic acids from β-Azol-substituted cinnamic esters 6.4 mmol of β-Azol-substituted methyl or ethyl cinnamates are suspended in a solution of 0.77 g of NaOH in 50 ml of water and 10 ml of methanol, and the mixture is stirred at room temperature until the TLC (mobile phase n-heptane/ethyl acetate) shows complete conversion and a clear solution has resulted. The latter is concentrated in vacuo, diluted with about 50 ml of water and, while cooling in ice, adjusted to pH 2–3 with 2N HCl. If a solid precipitates, it is filtered off with suction and dried in vacuo. Otherwise, the mixture is extracted several times with $CH_2Cl_2$, the organic phases are dried and evaporated in vacuo, and the residue is purified by recrystallization or chromatography on silica gel (mobile phase: n-heptane/ethyl acetate/glacial acetic acid).

The invention further relates to pharmaceuticals which contain one or more compounds of the formula I according to the invention and/or their pharmacologically compatible salts.

The pharmaceuticals are produced by processes known per se and familiar to the skilled worker. As pharmaceuticals, the pharmacologically active compounds (=active substance) according to the invention are employed either as such or, preferably, in combination with suitable pharmaceutical auxiliaries in the form of tablets, coated tablets, capsules, suppositories, emulsions, suspensions, granules, powders, solutions or products with protracted release of active substance, with the content of active substance advantageously being 0.1 to 95%.

The skilled worker is familiar on the basis of his expert knowledge with the auxiliaries which are suitable for the desired pharmaceutical formulation. Besides solvents, gel formers, suppository bases, tablet auxiliaries and other active substance excipients, it is possible to use, for example, antioxidants, dispersants, emulsifiers, foam suppressants, flavorings, preservatives, solubilizers or colorants.

The active substances can be administered topically, orally, parenterally or intravenously, with the preferred mode of administration depending on the disease to be treated. Oral administration is preferred.

For a form for oral use, the active compounds are mixed with the additives suitable therefor, such as excipients, stabilizers or inert diluents and converted by conventional methods into suitable administration forms such as tablets, coated tablets, hard gelatin capsules, aqueous, alcoholic or oily suspensions or aqueous, alcoholic or oily solutions. Examples or inert excipients which can be used are gum arabic, magnesia, magnesium carbonate, potassium phosphate, lactose, glucose or starch, especially corn starch. This preparation can take place either as dry or as wet granules. Suitable oily excipients or solvents are vegetable or animal oils, such as sunflower oil or fish liver oil.

For subcutaneous or intravenous administration, the active compounds or their physiologically tolerated salts are converted, if required with the substances customary for this purpose, such as solubilizers, emulsifiers or other auxiliaries, into a solution, suspension or emulsion. Examples of suitable solvents are water, physiological brine or alcohols, for example ethanol, propanol, glycerol, as well as sugar solutions such as glucose or mannitol solutions, or else a mixture of various solvents.

Pharmaceutical products suitable for topical and local use are eye drops which contain the active compound in aqueous or oily solution. Suitable for nasal use are aerosols and sprays as well as coarse powders which are administered by rapid inhalation through the nostrils and, in particular, nose drops which contain the active compounds in aqueous or oily solution.

The dosage of the active substance of the formula I to be administered, and the frequency of administration depend on the potency and duration of action of the compound according to the invention which is used; in addition on the nature and severity of the disease to be treated and on the sex, age, weight and individual response of the mammal to be treated. On average, the recommended daily dose of a compound according to the invention for a mammal weighing about 75 kg—primarily a human—is in the range of about 10 to 500 mg, preferably about 25 to 250 mg, it being possible for administration to take place in several doses a day as required.

The examples which follow are intended to illustrate the present invention without restricting its scope, however. anh means anhydrous; room temperature is about 18° to 25° C.

Example 1

Preparation of 1L-(1(OH),3,4-O-cyclohexylidene-5-tetrahydroxycyclohexanecarboxylic acid 1,5-lactone 2 from D-quinic acid 1

163.3 g (0.85 mol) of 1 were suspended in 186 ml (1.8 mol) of cyclohexanone. 0.5 ml of concentrated sulfuric acid was added. The mixture was then slowly heated to a heating bath temperature of 200° C., and a water/cyclohexanone azeotrope was distilled out. When no further azeotrope distilled over, the pale brown reaction solution was stirred at a bath temperature of 200° C. for a further 2 h. The reaction solution was then allowed to cool to 70° C., and 10 g of sodium bicarbonate were added. Subsequently 700 ml of ethyl acetate were added and the organic phase was washed with water and saturated sodium chloride solution. The organic phase was then concentrated in vacuo. The pale yellow residue was crystallized from isopropanol/water 1:1 to result in 142.1 g (75%) of lactone 2 as colorless crystals. m.p.: 140°–141° C.

Preparation of
[1R,2R,3R,5S]-1,2-O-cyclohexylidene-5-phenylmethoxy-3,5-lactonylcyclohexane-1,2-diol
(3, $R^2$=O—$CH_2$Ph)

0.81 g (28 mmol) of sodium hydride (80% in mineral oil) was suspended in 14 ml of anh. dimethylformamide under argon and, at 0° C., 7.1 g (28 mmol) of alcohol 2 dissolved in 16 ml of anh. dimethylformamide were added dropwise. The mixture was then stirred at 25° C. for 1 h and subsequently, again at 0° C., 3.5 ml of benzyl bromide were added. The reaction mixture was left to stir at room temperature for 4 h and then, at 0° C., saturated ammonium chloride solution was added. The mixture was extracted with ethyl acetate, and the combined organic phases were washed with saturated sodium chloride solution and dried with sodium sulfate. The residue after concentration in vacuo was recrystallized from n-heptane/methyl-tert-butyl ether (5:1). 7.18 g (75%) of benzyl ether 3 ($R^2$=O—$CH_2$ph) were obtained as colorless crystals. M.p.: 122°–126° C.

Preparation of sodium
[1S,3R,4R,5S]-3-hydroxy-4,5-O-cyclohexylidene-1-phenylmethyloxycyclohexanecarboxylate 4
($R^2$=O—$CH_2$Ph) from 3 ($R^2$=O—$CH_2$Ph)

3.1 g (9 mmol) of lactone 3 ($R^2$=O—$CH_2$Ph) were dissolved in 20 ml of dioxane and, at room temperature, 9.5 ml of 1N sodium hydroxide solution were added. The emulsion was left to stir at room temperature for 4 hours and subsequently concentrated in vacuo, and the colorless residue was dried over potassium hydroxide under high vacuum at 60° C. for 24 h. 3.32 g (96%) of the sodium salt 4 ($R^2$=O—$C_2$Ph) were obtained as a colorless solid. M.p.: 276°–279° C. (decomposition).

Preparation of
[1S,3R,4R,5S]-3-[(E)-3-(4-(trimethylsilylethoxymethoxyphenyl)propenoyl]
oxy-4,5-O-cyclohexylidene)1-phenylmethyloxycyclohexanecarboxylic acid 6 ($R^2$=O—$CH_2$Ph) from 4 ($R^2$=O—$CH_2$Ph)

a) Preparation of (E)-3-(4-trimethylsilylethoxymethoxyphenyl)-2-propenoic acid imidazolide 5 ($R^a$=imidazolyl)

a) 1.62 g (5.5 mmol) of (trimethylsilylethoxymethoxyphenyl)propenoic acid 5 ($R^a$=OH, Z=CH=CH, $R^3$ (protected=4-(trimethylsilylethoxymethoxyphenyl)) were dissolved in 10 ml of anh. dimethylformamide. At room temperature, a solution of 0.92 g (5.5 mmol) of carbonyldiimidazole dissolved in 10 ml of anh. dimethylformamide was added dropwise. This solution was then heated at 60°–70° C. for 1 h, during which evolution of $CO_2$ was observed.

b) 2.1 g (5.5 mmol) of 4 ($R^2$=O—$CH_2$Ph) were dissolved in 20 ml of anh. dimethylformamide. At 25° C. under argon, 165 mg (5.5 mmol) of sodium hydride (80% in mineral oil) were added. The mixture was stirred at 25° C. for 1 h, Subsequently, at 0° C., the solution of 5 prepared under a) was added dropwise. After 3 h at 0 to 5° C., the reaction mixture was poured into saturated ammonium chloride solution and extracted with ethyl acetate, and the combined organic phases were washed with saturated sodium chloride solution and dried with magnesium sulfate. The residue from concentration in vacuo was chromatographed on silica gel (mobile phase: ethyl acetate/n-heptane/glacial acetic acid 20:60:1). 2.5 g (71%) of ester 6 ($R^2$=O—$CH_2$Ph, Z=CH=CH, (protected)=4-(trimethylsilylethoxymethoxyphenyl)) were obtained as a colorless oil.

Preparation of
[1S,3R,4R,5S]-3-[(E)-3-(4-hydroxyphenyl)2-propenoyl]oxy-4,5-dihydroxy-1-phenylmethyloxycyclohexanecarboxylic acid 7
($R^3$=4-hydroxyphenyl, Z=CH=CH, $R^2$=phenylmethyloxy) from 6

2.7 g (7.0 mmol) of 6 were dissolved in 130 ml of dioxane and, while stirring at room temperature, 95 ml (0.19 mol) of 2N hydrochloric acid were added. The mixture was stirred at room temperature for 20 h. After the end of the reaction, the clear solution was adjusted to pH 3–4 with 2N sodium hydroxide solution and concentrated in vacuo. The solid residue was stirred in ethyl acetate with heating, and the insoluble sodium chloride was filtered off. The filtrate was again concentrated, and the residue was stirred with methyl tert-butyl ether. The residue was filtered off with suction and dried under high vacuum. 2.0 g (70%) of [1S,3R,4R,5S]-3(E)-3-(4 -hydroxyphenyl)-2-propenoyl]oxy-4,5-dihydroxy-1-phenylmethyloxycyclohexanecarboxylic acid 7 were obtained as a colorless solid. M.p.: 209°–212° C.

The following compounds were prepared in an analogous manner:

Example 2

[1S,3R,4R,5S]-3-[(E)-3-(4-hydroxyphenyl)-2-propenoyl]oxy-4,5-dihydroxy-1-(2-thienylmethyl)oxycyclohexanecarboxylic acid m.p.: 140° C.

Example 3

[1S,3R,4R,5S]-3-[(E)-3-(4-hydroxyphenyl)-2-propenoyl]oxy-4,5-dihydroxy-1-(2-propynyl)oxycyclohexanecarboxylic acid m.p.: 197° C.

Example 4

[1S,3R,4R,5S]-1-(4-chlorophenylpropyl)oxy-4,5-dihydroxy-3-(2-pyridinecarbonyl)oxycyclohexanecarboxylic acid m.p.: 128°–130° C.

Example 5

[1S,3R,4R,5S]-1-(4-chlorophenylpropyl)oxy-3-[(E)-3-(4-hydroxyphenyl)-2-propenoyl]oxy-4,5-dihydroxycyclohexanecarboxylic acid m.p.: 215°–219° C.

Example 6

[1S,3R,4R,5S]-1-methoxy-3-[(E)-3-(4-hydroxyphenyl)-2-propenoyl]oxy-4,5-dihydroxycyclohexanecarboxylic acid m.p.: 242°–243° C.

Example 7

[1S,3R,4R,5S]-1-ethoxy-3-[(E)-3-(4-hydroxyphenyl)-2-propenoyl]oxy-4,5-dihydroxycyclohexanecarboxylic acid m.p.: 227°–228° C. Example 8

[1S,3R,4R,5S]-3-[(E)-3-(4-hydroxyphenyl)-2-propenoyl]oxy-4,5-dihydroxy-1-propyloxycyclohexanecarboxylic acid m.p.: 221° C.

Example 9

[1S,3R,4R,5S]-1-(3-phenylpropyl)oxy-3-[(E)-3-(4-hydroxyphenyl)-2-propenoyl]oxy-4,5-dihydroxycyclohexanecarboxylic acid m.p.: 203° C.

Example 10

[1S,3R,4R,5S]-1-(4-chlorophenylmethyl)oxy-3-[(E)-3-(4-hydroxyphenyl)-2-propenoyl]oxy-4,5-dihydroxycyclohexanecarboxylic acid m.p.: 211° C.

Example 11

[1S,3R,4R,5S]-1-(4-methylphenylmethyl)oxy-3-[(E)-3-(4-hydroxyphenyl)-2-propenoyl]oxy-4,5-dihydroxycyclohexanecarboxylic acid m.p.: 198° C.

Example 12

[1S,3R,4R,5S]-1-(4-trifluoromethylphenylmethyl)oxy-3-[(E)-3-(4-hydroxyphenyl)-2-propenoyl]oxy-4,5-dihydroxycyclohexanecarboxylic acid m.p.: 195°–200° C.

Example 13

[1S,3R,4R,5S]-1-(4-biphenylmethyl)oxy-3-[(E)-3-(4-hydroxyphenyl)-2-propenoyl]oxy-4,5-dihydroxycyclohexanecarboxylic acid m.p.: 222° C.

Example 14

[1S,3R,4R,5S]-1-(1-naphthylmethyl)oxy-3-[(E)-3-(4-hydroxyphenyl)-2-propenoyl]oxy-4,5-dihydroxycyclohexanecarboxylic acid m.p.: 165°–170° C.

Example 15

[1S,3R,4R,5S]-1-(2-naphthylmethyl)oxy-3-[(E)-3-(4-hydroxyphenyl)-2-propenoyl]oxy-4,5-dihydroxycyclohexanecarboxylic acid m.p.: 198° C.

Example 16

[1S,3R,4R,5S]-1-(3-methoxyphenylmethyl)oxy-3-[(E)-3-(4-hydroxyphenyl)-2-propenoyl]oxy-4,5-dihydroxycyclohexanecarboxylic acid m.p.: 189°–191° C.

Example 17

[1S,3R,4R,5S]-1-(4-fluorophenylmethyl)oxy-3-[(E)-3-(4-hydroxyphenyl)-2-propenoyl]oxy-4,5-dihydroxycyclohexanecarboxylic acid m.p.: 214° C.

Example 18

[1S,3R,4R,5S]-1-(4-cyanophenylmethyl)oxy-3-[(E)-3-(4-hydroxyphenyl)-2-propenoyl]oxy-4,5-dihydroxycyclohexanecarboxylic acid m.p.: 238°–241° C.

Example 19

[1S,3R,4R,5S]-1-(3-(3-methoxyphenyl)propyl)oxy-3-[(E)-3-(4-hydroxyphenyl)-2-propenoyl]oxy-4,5-dihydroxycyclohexanecarboxylic acid m.p.: 208°–210° C.

Example 20

[1S,3R,4R,5S]-1-((E)-3-(4-chlorophenyl)-2-propenyl)oxy-3-[(E)-3-(4-hydroxyphenyl)-2-propenoyl]oxy-4,5-dihydroxycyclohexanecarboxylic acid m.p.: 170°–173° C.

Example 21

[1S,3R,4R,5S]-1-((3-chlorophenyl)propyl)oxy-3-[(E)-3-(4-hydroxyphenyl)-2-propenoyl]oxy-4,5-dihydroxycyclohexanecarboxylic acid m.p.: 211° C.

Example 22

[1S,3R,4R,5S]-1-(4-phenylbutyl)oxy-3-[(E)-3-(4-hydroxyphenyl)-2-propenoyl]oxy-4,5-dihydroxycyclohexanecarboxylic acid m.p.: 217° C.

Example 23

[1S,3R,4R,5S]-1-(3,3-diphenylpropyl)oxy-3-[(E)-3-(4-hydroxyphenyl)-2-propenoyl]oxy-4,5-dihydroxycyclohexanecarboxylic acid m.p.: 155°–160° C.

Example 24

Sodium [1S,3R,4R,5S]-1-(3-(4-tert-butylphenyl)methyl)oxy-3-[(E)-3-(4-hydroxyphenyl)-2-propenoyl]oxy-4,5-dihydroxycyclohexanecarboxylate m.p.: 80°–90° C.

Example 25

[1S,3R,4R,5S]-1-(3-(4-chloro-2-methoxyphenyl)propyl)oxy-3-[(E)-3-(4-hydroxyphenyl)-2-propenoyl]oxy-4,5-dihydroxycyclohexanecarboxylic acid m.p.: 190°–194° C.

Example 26

[1S,3R,4R,5S]-1-(3-(5-chloro-2-methoxyphenyl)propyl)oxy-3-[(E)-3-(4-hydroxyphenyl)-2-propenoyl]oxy-4,5-dihydroxycyclohexanecarboxylic acid m.p.: 215°–218° C.

Example 27

[1S,3R,4R,5S]-1-(3-(4-chlorophenyl)-2-propynyl)oxy-3-[(E)-3-(4-hydroxyphenyl)-2-propenoyl]oxy-4,5-dihydroxycyclohexanecarboxylic acid m.p.: 233°–234° C.

Example 28

[1S,3R,4R,5S]-1-[3,3-di(4-chlorophenyl)propyl]oxy-3-[(E)-3-(4-hydroxyphenyl)-2-propenoyl]oxy-4,5-dihydroxycyclohexanecarboxylic acid m.p.: 122°–126° C.

Example 29

[1S,3R,4R,5S]-1-((E)-3-(2-chlorophenyl)-2-propenyl)oxy-3-[(E)-3-(4-hydroxyphenyl)-2-propenoyl]oxy-4,5-dihydroxycyclohexanecarboxylic acid m.p.: 192°–196° C.

Example 30

[1S,3R,4R,5S]-1-(4-phenoxybutyl)oxy-3-[(E)-3-(4-hydroxyphenyl)-2-propenoyl]oxy-4,5-dihydroxycyclohexanecarboxylic acid m.p.: 194°–195° C.

Example 31

[1S,3R,4R,5S]-1-(3-(3,4-dichlorophenyl)propyl)oxy-3-[(E)-3-(4-hydroxyphenyl)-2-propenoyl]oxy-4,5-dihydroxycyclohexanecarboxylic acid m.p.: 213°–215° C.

Example 32

[1S,3R,4R,5S]-1-(4-(4-chlorophenyl)butyl)oxy-3-[(E)-3-(4-methoxyphenyl)-2-propenoyl]oxy-4,5-dihydroxycyclohexanecarboxylic acid m.p.: 77°–82° C.

Example 33

[1S,3R,4R,5S]-1-(3-(4-chlorophenyl)propyl)oxy-3-[(E)-3-(4-methoxyphenyl)-2-propenoyl]oxy-4,5-dihydroxycyclohexanecarboxylic acid MS: m/e=505 (M+H$^+$)

Example 34

[1S,3R,4R,5S]-1-(3-(4-chlorophenyl)propyl)oxy-3-[(E)-3-(2-methoxyphenyl)-2-propchoyl]oxy-4,5-dihydroxycyclohexanecarboxylic acid MS: m/e=505 (M+H$^+$)

Example 35

[1S,3R,4R,5S]-1-(4-(3-(2-ethoxycarbonylthienyl)oxy)butyl)oxy-3-[(E)-3-(4-hydroxyphenyl)-2-propenoyl]oxy-4,5-dihydroxycyclohexanecarboxylic acid m.p.: 144°–147° C.

Example 36

[1S,3R,4R,5S]-1-(3-(2-thienyl)propyl)oxy-3-[(E)-3-(4-hydroxyphenyl)-2-propenoyl]oxy-4,5-dihydroxycyclohexanecarboxylic acid m.p.: 211°–213° C.

Example 37

[1S,3R,4R,5S]-1-(2-thienyl)methyloxy-3-[(E)-3-(4-hydroxyphenyl)-2-propenoyl]oxy-4,5-dihydroxycyclohexanecarboxylic acid m.p.: 140° C. (decomp.)

Example 38

[1S,3R,4R,5S]-1-(2-thienyl)methyloxy-3-[(E)-3-(3-methoxythienyl)-2-propenoyl]oxy-4,5-dihydroxycyclohexanecarboxylic acid MS: m/e=455 (M+H$^+$)

Example 39

[1S,3R,4R,5S]-1-(3-(3-thienyl)methyl)oxy-3-[(E)-3-(4-hydroxyphenyl)-2-propenoyl]oxy-4,5-dihydroxycyclohexanecarboxylic acid m.p.: 156°–160° C.

Example 40

[1S,3R,4R,5S]-1-[3-(2-(5-chlorothienyl))propyl]oxy-3-[(E)-3-(4-hydroxyphenyl)-2-propenoyl]oxy-4,5-dihydroxycyclohexanecarboxylic acid m.p.: 215°–218° C.

Example 41

[1S,3R,4R,5S]-1-4-(3,5-dimethyldithieno(3,2-b:3',2'-e)pyridinyl)butyloxy-3-[(E)-3-(4-hydroxyphenyl)-2-propenoyl]oxy-4,5-dihydroxycyclohexanecarboxylic acid m.p.: 240°–244° C.

Example 42

[1S,3R,4R,5S]-1-[(3,5-dimethyldithieno(3,2-b:3',2'-e)pyridinyl)methyl]oxy-3-[(E)-3-(4-hydroxyphenyl)-2-propenoyl]oxy-4,5-dihydroxycyclohexanecarboxylic acid m.p.: 240°–244° C.

Example 43

[1S,3R,4R,5S]-1-(3-(3-thienyl)propyl)oxy-3-[(E)-3-(4-hydroxyphenyl)-2-propenoyl]oxy-4,5-dihydroxycyclohexanecarboxylic acid m.p.: 211°–213° C.

Example 44

[1S,3R,4R,5S]-1-(4-chlorophenylpropyl)oxy-3-[(E)-3-(4-hydroxyphenyl)propoyl]oxy-4,5-dihydroxycyclohexanecarboxylic acid m.p.: 157°–159° C.

A number of other compounds were prepared by process C.
1. Alkylation 30.0 g (0.118 mol) of lactone 2 were dissolved in 200 ml of anh. dimethylformamide. At room temperature under an argon atmosphere, 5.3 g (0.176 mol) of sodium hydride (80% in mineral oil) were added. After 1.5 h, the mixture was cooled to 0°–10° C. and 20 ml (0.265 mol) of propargyl bromide were added dropwise over 30 min. The solution slowly became dark in color. After 1 h (TLC check) the reaction mixture was poured into half-saturated ammonium chloride solution. The mixture was extracted with ethyl acetate, and the organic phase was washed with saturated sodium chloride solution and dried with magnesium sulfate. The residue after concentration in vacuo was filtered through 1 kg of silica gel(mobile phase: ethyl acetate/n-heptane 1:5). 30.0 g (87%) of propargyl ether 3' ($R^2$=propynyloxy) were obtained as a viscous oil.

2nd stage: Coupling 24.0 g (0.082 mmol) of propargyl ether 3'($R^2$=propynyloxy) were dissolved in 150 ml of anhydrous toluene and 50 ml of anhydrous triethylamine. Under an argon atmosphere, 0.354 g (0.002 mmol) of palladium dichloride, 1.05 g (0.004 mmol) of triphenylphosphine, 19.55 g (0.082 mol) of 4-chloroiodobenzene and 0.050 g (0.0003 mmol) of copper(I) iodide were successively added. The reaction solution was slowly heated to 80° C. and the reaction mixture was left at this temperature for 4 hours. It was subsequently cooled to room temperature, the resulting triethylammonium hydrobromide was filtered off, and the precipitate was washed with ethyl acetate. The filtrate was concentrated in vacuo, and the viscous oily residue was purified by chromatography on 1 kg of silica gel (mobile phase: EA/n-heptane 1:5; dissolve residue in a little ethyl acetate for loading onto the silica gel). 23.0 g (69%) of phenylpropynyl ether 3" ($R^2$=3-(4 -chlorophenyl)-2-propynyloxy), which was recrystallizable from methylcyclohexane, were obtained. M.p.: 79° C.

Preparation of alkene 3''' ($R^2$=3-(4-chlorophenyl)-2-propenyloxy) from alkyne 3" ($R^2$=3-(4-chlorophenyl)-2-propynyloxy):

12.0 g (29.8 mmol) of alkyne 3" ($R^2$=3-(4-chlorophenyl)-2-propynyloxy) were dissolved in 300 ml of pyridine, and 3.0 g of palladium on barium sulfate(10% palladium) were added. The suspension was shaken under a hydrogen atmosphere at 25° C. for 4 h. After hydrogen uptake ceased, the catalyst was filtered off and the pyridine solution was concentrated in vacuo. 11.2 g (93%) of alkene 3''' ($R^2$=3-(4-chlorophenyl)propenyloxy) were obtained as a colorless solid. M.p.: 155°–157° C.

The other reaction steps were carried out in analogy to process A(steps from 3 to 7).

Preparation of alkane $3^{IV}$ ($R^2$=3-(4-chlorophenyl)propyloxy) from alkyne 3''' ($R^2$=3-(4-chlorophenyl)propynyloxy): 6.0 g (14.9 mmol) of alkyne 3 ($R^2$=3-(4-chlorophenyl)-2-propynyloxy) were dissolved in 50 ml of ethanol/ethyl acetate(1:4), and 1.0 g of rhodium on aluminum oxide(5% rhodium) was added. The reaction mixture was shaken under a hydrogen atmosphere at room temperature for about 15 h. The catalyst was then filtered off, and the filtrate was concentrated in vacuo. 6.05 g (100%) of alkane $3^{IV}$ ($R^2$3-(4-chlorophenyl)propyloxy) were obtained as a colorless oil.

The alkanes 3 obtainable in this way were also reacted further as in process A (steps-from 3 to 7).

Example 45

[1S,3R,4R,5S]-1-(3-(4-fluorophenyl)propyl)oxy-3-[(E)-3-(4-hydroxyphenyl)-2-propenoyl]oxy-4,5-dihydroxycyclohexanecarboxylic acid m.p.: 140°–170° C.

Example 46

[1S,3R,4R,5S]-1-((Z)-3-(4-chlorophenyl)-2-propenyl)oxy-3-[(E)-3-(4-hydroxyphenyl)-2-propenoyl]oxy-4,5-dihydroxycyclohexanecarboxylic acid m.p.: 208°–209° C.

Example 47

[1S,3R,4R,5S]-1-((Z)-3-(5-pyrimidyl)-2-propenyl)oxy-3-[(E)-3-(4-methoxyphenyl)-2-propenoyl]oxy-4,5 dihydroxycycloyhexanecarboxylic acid m.p.: 75°–78° C.

Example 48

[1S,3R,4R,5S]-1-((Z)-3-(5-pyrimidyl)-2-propenyl)oxy-3-[(E)-3-(4-methoxyphenyl)-2-propenoyl]oxy-4,5-O-cyclohexylidenecyclohexanecarboxylic acid m.p.: 165°–167° C.

Example 49

[1S,3R,4R,5S]-1-((Z)-3-(2-naphthyl)-2-propenyl)oxy-3-[(E)-3-(4-methoxyphenyl)-2-propenoyl]oxy-4,5-dihydroxycyclohexanecarboxylic acid m.p.: 146°–149° C.

Example 50

[1S,3R,4R,5S]-1-((Z)-3-(3-trifluoromethylphenyl)-2-propenyl)oxy-3-[(E)-3-(4-hydroxyl)-2-propenoyl]oxy-4,5-dihydroxycyclohexanecarboxylic acid m.p.: 187°–190° C.

Example 51

Methyl
[1S,3R,4R,5S]-1-(3-(4-chlorophenyl)propyl)oxy-3-[(E)-3-(4-methoxyphenyl)-2-propenoyl]oxy-4,5-dihydroxycyclohexanecarboxylate MS: m/e=505 (M+H$^+$)

Example 52

[1S,3R,4R,5S]-1-(3-(4-chlorophenyl)propyl)oxy-3-[(E)-3-phenyl-2-propenoyl]oxy-4,5-dihydroxycyclohexanecarboxylic acid MS: m/e=475 (M+H$^+$)

Example 53

[1S,3R,4R,5S]-1-(3-(4-chlorophenyl)propyl)oxy-3-[(E)-3-(3,4-dichlorophenyl-2-propenoyl]oxy-4,5-dihydroxycyclohexanecarboxylic acid MS: m/e=543 (M+H$^+$)

Example 54

[1S,3R,4R,5S]-1-(3-(4-chlorophenyl)propyl)oxy-3-[(E)-2-phenyl-1-cyclopropylcarbonyl]oxy-4,5-dihydroxycyclohexanecarboxylic acid MS: m/e=489(M+H$^+$)

Example 55

[1S,3R,4R,5S]-1-(3-(4-chlorophenyl)propyl)oxy-3-[3-(4-hydroxyphenyl)propoyl]oxy-4,5-dihydroxycyclohexanecarboxylic acid MS: m/e=493 (M+H$^+$)

Example 56

[1S,3R,4R,5S]-1-(3-(4-chlorophenyl)propyl)oxy-3-[3-(4-methoxyphenyl)propoyl]oxy-4,5-dihydroxycyclohexanecarboxylic acid MS: m/e=507 (M+H$^+$)

Example 57

[1S,3R,4R,5S]-1-(2-(4-chlorophenyl)-1-cyclopropylenemethylenemethyl)oxy-3-[(E)-3-(4-hydroxyphenyl)-2-propenoyl]oxy-4,5-dihydroxycyclohexanecarboxylic acid m.p.: 195°–199° C.

Examples for variation of the radicals R$^4$ and R$^5$ by process B
Preparation of lactone diol 8 (R$^2$=—O—CH—CH=CH—(p-Cl-phenyl), cis) from 3 (R$^2$=—O—CH—CH=CH—(p-Cl-phenyl), cis):

11.0 g (27.7 mmol) of lactone 3 (R$^2$=—O—CH—CH=CH—(p-Cl-phenyl), cis) were dissolved in isopropanol. 40 ml of 2N hydrochloric acid were added. The reaction solution was left to stand at room temperature for 48 hours and was subsequently neutralized with 1N sodium hydroxide solution and concentrated in vacuo, and the residue was chromatographed on silica gel. 7.8 g (90%) of lactone diol 8 (R$^2$=—O—CH—CH=CH—(p-Cl-phenyl), cis) were obtained as a colorless solid. M.p.: 117°–120° C.
Preparation of the 5-tert-butyldimethylsilyloxy compound 9 (R$^2$=—O—CH—CH=CH—(p-Cl-phenyl), cis) from the lactone diol 8 (R$^2$=—O—CH—CH=CH—(p-Cl-phenyl), cis):

5.0 g (15.4 mmol) of lactone diol 8 (R$^2$=—O—CH—CH=CH—(p-Cl-phenyl), cis) and 4.15 g (61.9 mmol) of imidazole were dissolved in 50 ml of anh. dimethylformamide. At 0° C., 3.9 g (26 mmol) of tert-butyldimethylsilyl chloride were added. After 4 h, saturated ammonium chloride solution was added to the reaction mixture, and the latter was extracted with methyl tert-butyl ether. The combined organic phases were dried with magnesium sulfate and concentrated in vacuo. The residue was purified on silica gel(mobile phase: ethyl acetate/n-heptane 1:3). 5.7 g (84%) of silyl ether 9 (R$^2$=—O—CH—CH=CH—(p-Cl-phenyl), cis) were obtained as a colorless solid. M.p.: 71° C.

It is also possible in this way by carrying out the reaction at room temperature to produce a mixture of the two silyl ethers 9 and 10 which can be separated by chromatography on silica gel using the abovementioned solvent mixture.
Preparation of 3,3-di(4-chlorophenyl)-2-propenyl ether 11 (R$^2$=—O—CH—CH=CH—(p-Cl-phenyl), cis) from 9 (R$^2$=—O—CH—CH=CH—(p-Cl-phenyl), cis).

1.0 g (2.3 mmol) of alcohol 9 (R$^2$=—O—CH—CH=CH—(p-Cl-phenyl), cis) was dissolved in 20 ml of anhydrous dimethylformamide. At room temperature under argon, 150 mg (5 mmol) of sodium hydride(80% in mineral oil) were added, and the mixture was stirred for 1 h. It was subsequently cooled to 0° C. and 0.85 g (3.2 mmol) of 3,3-di(4-chlorophenyl)-2-propenyl bromide dissolved in 5 ml of anhydrous dimethylformamide was added, and the reaction mixture was allowed to warm to room temperature. After 14 h, saturated ammonium chloride solution was added to the reaction mixture, and the latter was extracted with methyl tert-butyl ether. The combined organic phases were dried with magnesium sulfate and concentrated in vacuo. The residue was purified on silica gel(mobile phase: ethyl acetate/n-heptane 1:3). 0.5 g (84%) of ether 11 (R$^2$=—O—CH—CH=CH—(p-Cl-phenyl), cis) was obtained as a colorless oil.

11 was reacted in analogy to process A to give the compound of Example 58:

Example 58

[1S,3R,4R,5S]-1-((Z)-3-(4-chlorophenyl)-2-propenyl)oxy-3-[(E)-3-(4-hydroxyphenyl)propoyl]oxy-4-[3,3-di(4-chlorophenyl-2-propenyl]oxy-5-dihydroxycyclohexanecarboxylic acid m.p.: 157°–161° C.

Example 59 was also synthesized in analogy to Example 58:

Example 59

Sodium [1S,3R,4R,5S]-1-((Z)-3-(4-chlorophenyl)-2-propenyl)oxy-3-[(E)-3-(4-hydroxyphenyl)propoyl]oxy-4-phenylmethyloxy-5-dihydroxycyclohexanecarboxylate $^1$H-NMR (270 MHz, d$_6$-DMSO): d=1.85–2.3 ppm (m, 3H), 3.3–3.5 (m, 2H), 4.05–4.70 (m, 6H), 5.2–5.38 (m, 1H), 5.82–5.93 (m, 1H), 6.3 (d, J=10.0 Bz, 1H), 6.42–6.5 (m, 1H), 6.75–6.85 (m, 2H), 7.2–7.55 (m, 12H), 11 ppm (1H).

The compounds of the following examples were prepared in a manner analogous to that described in Example 1:

Example 60

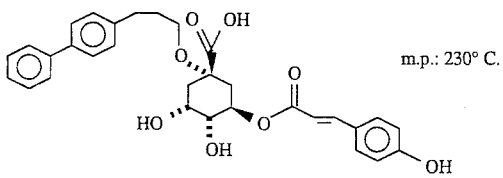

m.p.: 230° C.

Example 61

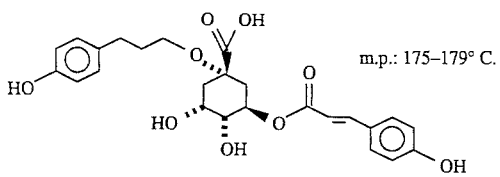

m.p.: 175–179° C.

Example 62

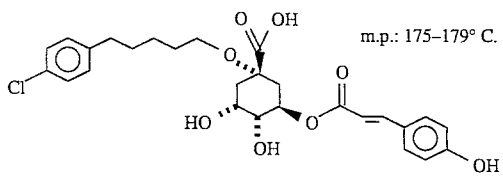

m.p.: 175–179° C.

Example 63

1) 68 ml of 1.2M diisobutylaluminumhydride were added to 30.0 g (73.7 mmol) of 63A

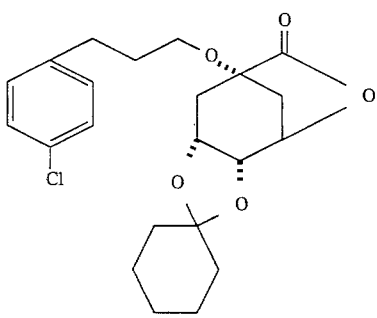

in 250 ml of anh. toluene under an argon atmosphere at −50° to −60° C. After 1 h, at −60° C. 50 ml of a methanol/water mixture (9:1) were added dropwise. The reaction mixture was warmed to 0° C. Subsequently the reaction mixture was poured into 1N potassium bisulfate solution (pH~4) and extracted with EA, and the organic phase was dried with sodium sulfate.

Concentration resulted in 30.0 g of 63B

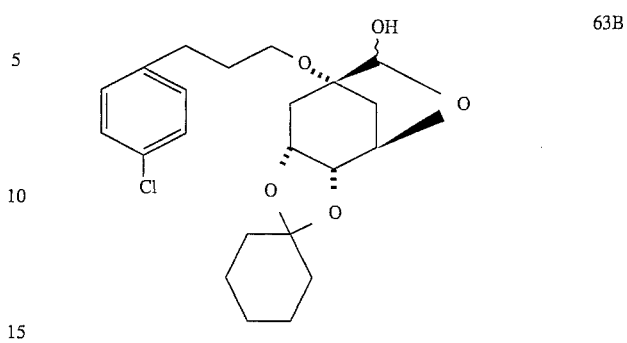

which was reacted further without purification.

2) 19.8 g (88.1 mmol) of triethyl phosphonoacetate were dissolved in 200 ml of anh. tetrahydrofuran. At 0 to 5° C. under an argon atmosphere, 2.65 g of 80% sodium hydride were added in portions. The result after 20 min was a clear brownish solution to which, at −40° to −50° C., 30.0 g (73.4 mmol) of 63B dissolved in 100 ml of anh. tetrahydrofuran were added dropwise. After 4 h at −20° to −30° C., the reaction mixture was poured into saturated ammonium chloride solution and extracted with ethyl acetate, and the combined organic phases were dried with sodium sulfate and concentrated in vacuo. Purification of the residue by chromatography on silica gel resulted in 22.3 g of 63C

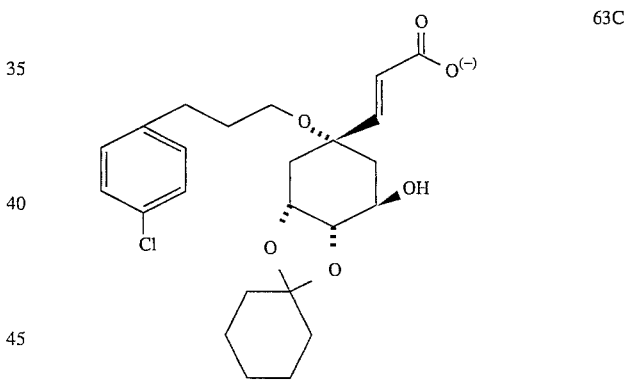

as a colorless oil.

3) 63C was converted by processes known to the skilled worker into 63D

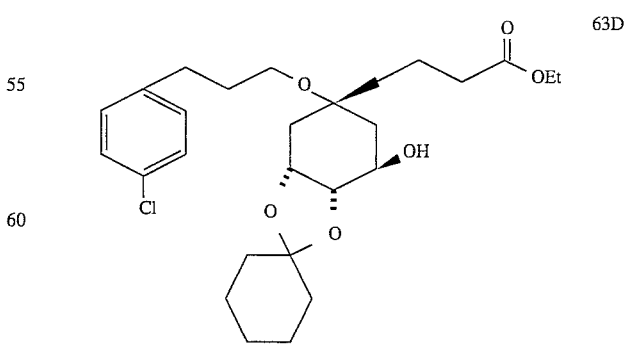

and reacted further in analogy to Example 1 (stage b and 6→7) to give 63 of the formula

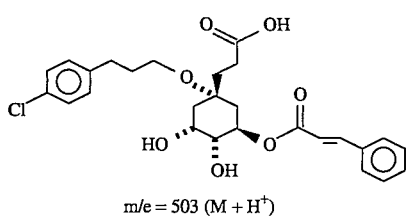

m/e = 503 (M + H⁺)

The compounds of the following examples were prepared in analogy to Example 1:

Example 64

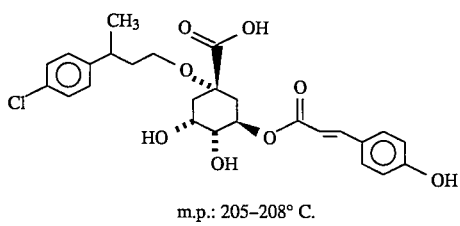

m.p.: 205–208° C.

Example 65

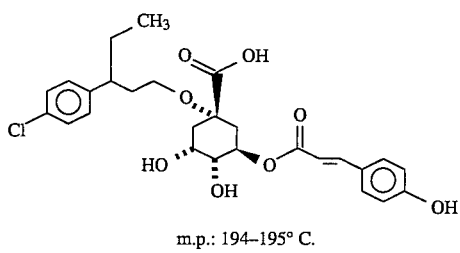

m.p.: 194–195° C.

Example 66

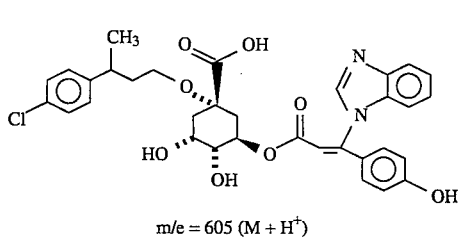

m/e = 605 (M + H⁺)

Example 67

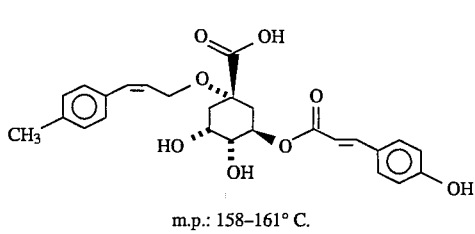

m.p.: 158–161° C.

Example 68

1) 15 ml of 2M diethylzinc solution in toluene were introduced at 0° C. in 150 ml of anhydrous dichloromethane and, under an argon atmosphere, 10.4 g (59.2 mmol) of chloroiodomethane were added dropwise, and the mixture was stirred at 0°–5° C. for 30 min. Subsequently, 6.0 g (14.8mmol of olefin) of 68A

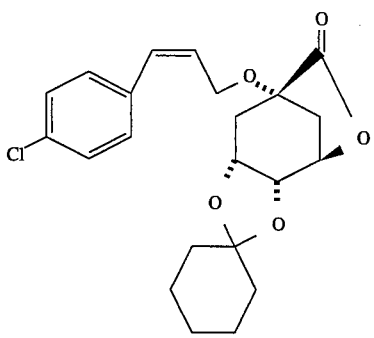

dissolved in 50 ml of anhydrous dichloromethane were added dropwise. The reaction solution was allowed to warm to 25° C. over the course of 2 h and was subsequently hydrolyzed with saturated ammonium chloride solution, followed by extraction with EA and concentration in vacuo. 5.5 g (91%) of cyclopropane derivative 68B were obtained, of the formulae

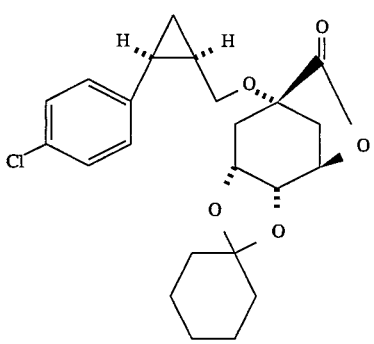

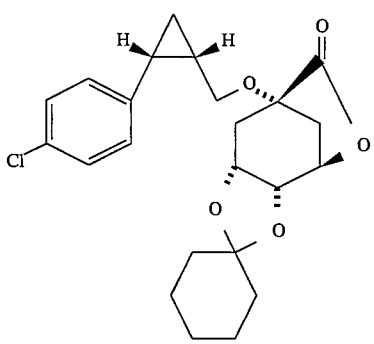

(3:1 mixture of the two possible diastereomers) which were separable by crystallization from i-propanol.

2) 2.0 g (4.8 mmol) of lactone 68B were dissolved in 50 ml of anhydrous toluene under an argon atmosphere and, at −60° C. 4.1 ml of 12M diisobutylaluminum hydride solution in toluene were added dropwise. The reaction solution was stirred at −60° C. for 2 h and then hydrolyzed with 10 ml of $H_2O$. Saturated ammonium chloride solution was added to this mixture, followed by extraction with ethyl acetate, drying with magnesium sulfate and concentration in vacuo.

2.0 g (99%) of lactol 68C of the formula

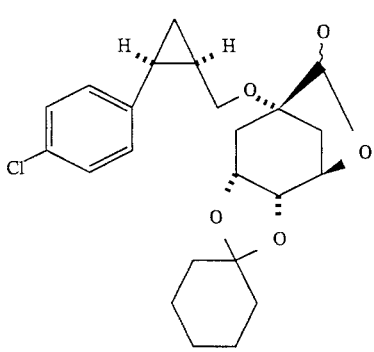

68C were obtained as a colorless oil.

3) 2.0 g (4.76 mmol) of 68C were dissolved in 50 ml of MeOH. A solution of 5.1 g of hydroxylamine hydrochloride and 5.0 g of potassium hydroxide in 50 ml of MeOH was added dropwise at 25° C. After stirring at 25° C. for 2 hours, the reaction solution was poured into water and extracted with methyl tert-butyl ether. The combined organic phases were dried with magnesium sulfate and concentrated in vacuo. The crude product 68D of the formula

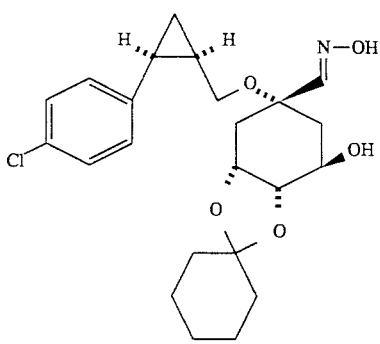

68D was reacted further without purification.

4) 2.1 g (4.8 mmol) of 68D were introduced into 50 ml of anhydrous dichloromethane and, at 25° C., 4.6 g (12.3 mmol) of carbonyldiimidazole were added. The mixture was subsequently warmed at 40° C. for 3 h and, after $CO_2$ evolution had ceased, 100 ml of anh.

methanol were added and the mixture was again heated at 40° C. for 4 h. It was then concentrated in vacuo, the residue was taken up in methyl tert-butyl ether, and the organic phase was washed with 0.1N potassium bisulfate solution and dried with magnesiumsulfate. The residue after concentration of the organic phase was purified by chromatography on silica gel(mobile phase: ethyl acetate/n-heptane 1:4) to result in 1.3 g of 68E of the formula

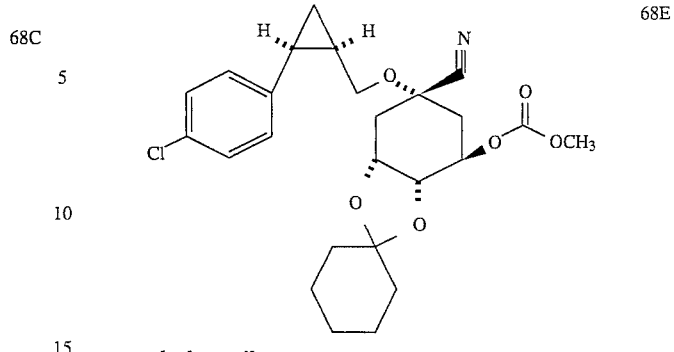

68E as a colorless oil.

5) The compound 68 of the formula

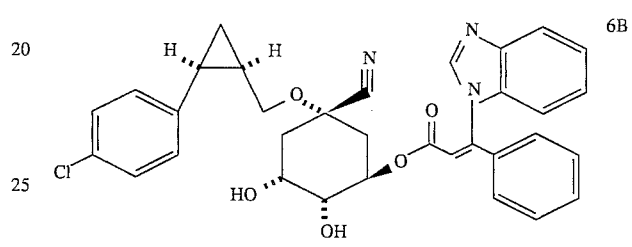

6B $m/3 = 584\ (M + H^+)$
m.p.: 197–202° C.

was obtained from 68E in analogy to the conversion 4→6 according to Example 1.

Example 69

The compound 69

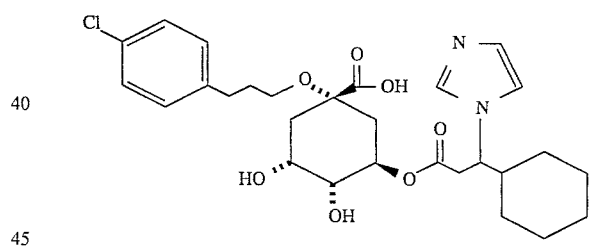

$m/e = 549\ (M + H^+)$ was prepaid in analogy to Example 1.

Example 70

Stage 1: Methyl 1-[4-(4-chlorophenyl)butyl]cyclohex-3-en-ecarboxylate 70B from 70A 85 mmol (11.9 ml) of dry diisopropylamine are dissolved in 200 ml of dry TBF and cooled under protective gas (nitrogen or argon) in a dry ice/acetone cooling bath. 80 mmol (50 ml) of a 1.6 molar solution of n-butyllithium in hexane are run into this while stirring vigorously. The mixture is stirred for 10 min and then 75 mmol (10.5 g) of methyl cyclohex-3-ene-1-carboxylate 70A

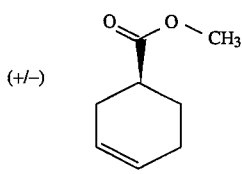

(commercially obtainable) dissolved in 10 ml of THF are added dropwise so that the internal temperature does not exceed −65° C. The mixture is subsequently stirred at −70° to −80° C. for 30 min and then 74 mmol (21.8 g) of 4-(4-chlorophenyl)butyl iodide dissolved in 25 ml of THF are added dropwise so that the internal temperature does not exceed −65° C. The mixture is subsequently stirred at −70° to −80° C. for 3 h and then the cooling bath is removed. After the internal temperature has reached 10° C., the reaction solution is stirred into 400 ml of saturated ammonium chloride solution and extracted 3x with MTB ether, the combined extracts are washed 3x with water and 2x with saturated brine and dried over sodium sulfate, and the solvent is removed in vacuo. The crude product is purified by flash chromatography on silica gel(mobile phase: ethyl acetate/n-heptane 1/9 vol/vol). The product 70B of the formula

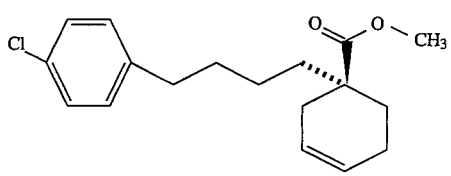

is obtained as a white low-melting wax.

Mass spectrum: m/e=307 (M+H⁺)

Stage 2: Sodium 1-[4-(4-chlorophenyl)butyl]cyclohex-3-ene-1-carboxylate 70C from 70B 22.7 g of methyl 1-[4-(4-chlorophenyl)butyl]cyclohex-3-ene-1-carboxylate 70B are dissolved in 100ml of methanol +100 ml of dioxane. To this is added a solution of 8 g of sodium hydroxide in 50 ml of water, and the mixture is refluxed under protective gas for 16 h. The reaction solution is cooled and 200 ml of water, 100 ml of toluene and 100 ml of n-heptane are added, and the mixture is stirred thoroughly. The precipitated product is filtered off with suction, washed with a little cold water and n-heptane/toluene (1:1 vol/vol) and dried in vacuo. 70C of the formula

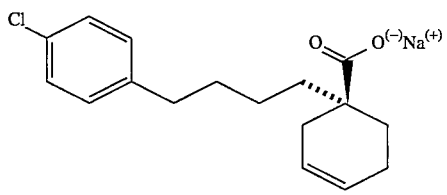

is obtained as colorless shining flakes which do not melt up to 240° C. The free acid obtained from the sodium salt 70C by acidification with concentrated hydrochloric acid melts at 86°–7° C.

Stage 3: 1-[4-(4-Chlorophenyl)butyl]-4-exo-iodo-6-oxabicyclo[3.2.1]octan-7-one 70D from 70C 22.2 g of sodium 1-[4-(4-chlorophenyl)butyl]cyclohex-3-ene-1-carboxylate 70C are suspended in a solution of 22 g of sodium bicarbonate and 68 g of potassium iodide in 350 ml of water. To this are added 175 ml of MTB ether and 20 g of iodine and the mixture is stirred under a protective gas at room temperature for 16 h. 10% strength aqueous sodium bisulfite solution is added in portions to the reaction solution until the iodine colour has disappeared, and the solution is extracted three times with ethyl acetate. The extracts are washed twice with saturated brine, dried over sodium sulfate and evaporated in vacuo. 70D of the formula

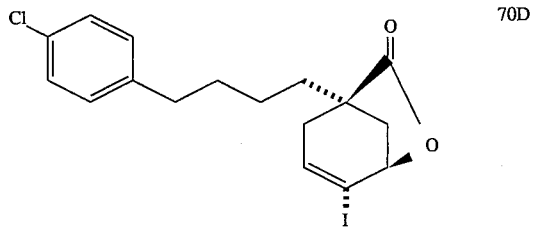

is obtained as a pale yellowish solid of melting point 84°–6° C.

Stage 4:1-[4-(4-Chlorophenyl)butyl]-6-oxabicyclo[3.2.1]-octan-7-one 70E from 70D 2 g of 1-[4-(4-chlorophenyl)butyl]-4-exo-iodo-6-oxabicyclo[3.2.1]octan-7-one 70D are dissolved in 20 ml of dry MTB ether. To this is added under a protective gas about 0.1 ml of a 1 molar solution of triethylborane in THF and then 1.35 ml of tributyltin hydride are added dropwise.

The mixture is stirred at room temperature for 2 h and then a solution of 5 g of potassium fluoride in 50 ml of water is added, and the mixture is stirred vigorously for 30 min. The precipitate which has separated out is filtered off with suction, the filtrate is extracted three times with MTB ether, the extracts are washed twice each with water and saturated brine and dried over sodium sulfate, and the solvent is distilled off in vacuo. The crude product is purified by flash chromatography on silica gel(mobile phase ethyl acetate/n-heptane ⅓ vol/vol). 70E

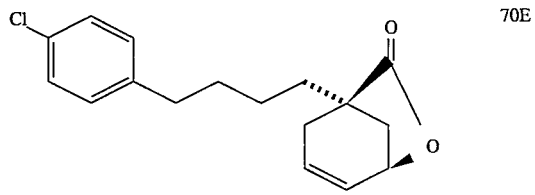

is obtained as a colorless oil which solidifies to a low-melting wax. Mass spectrum: m/e=293 (M+H⁺)

Stages 5 and 6 are carried out in analogy to Example 1.

The compound 70 of the formula

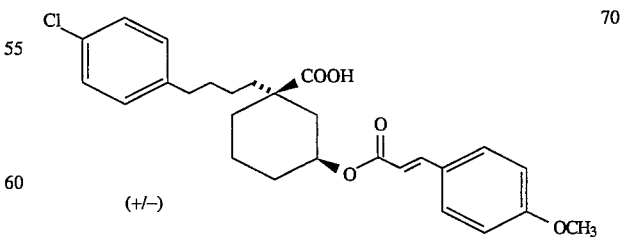

is obtained.

The compounds of the following examples were prepared in analogy to Example 1:

41
Example 71
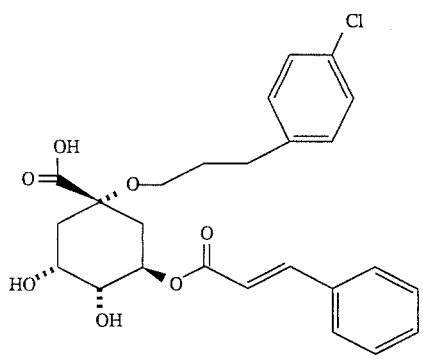
m/e = 475 (M + H⁺)
Example 72
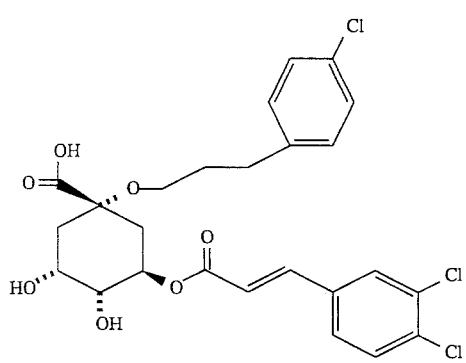
m/e = 543 (M + H⁺)
Example 73
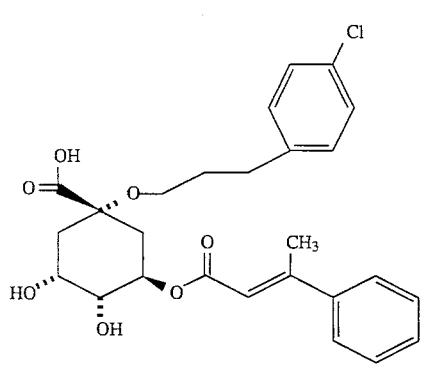
m/e = 488 (M + H⁺)
42
Example 74
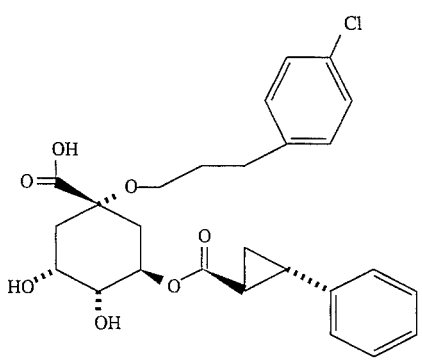
m/e = 489 (M + H⁺)
Example 75
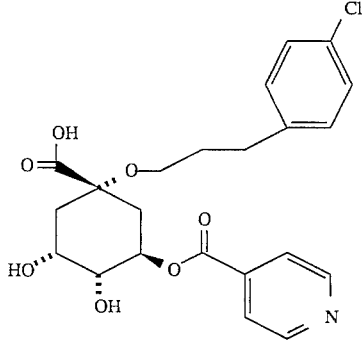
m/e = 450 (M + H⁺)
Example 76
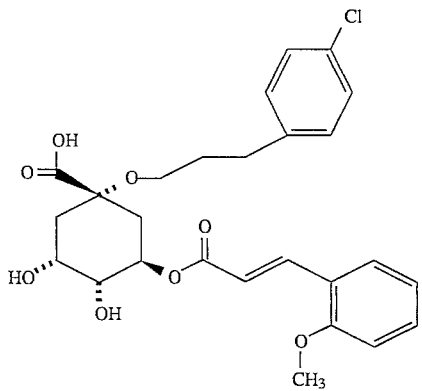
m/e = 505 (M + H⁺)

43
Example 77
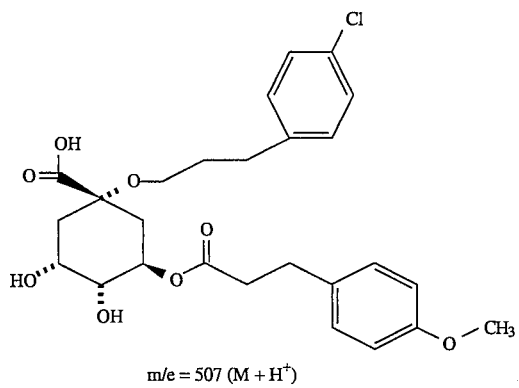
m/e = 507 (M + H⁺)
Example 78
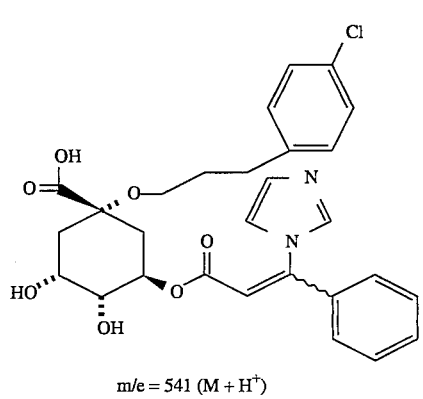
m/e = 541 (M + H⁺)
Example 79
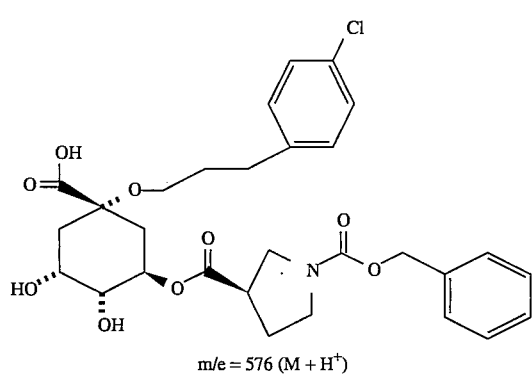
m/e = 576 (M + H⁺)
44
Example 80
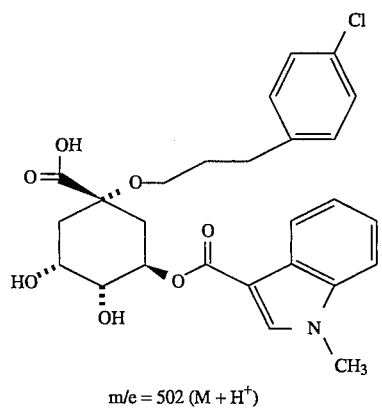
m/e = 502 (M + H⁺)
Example 81
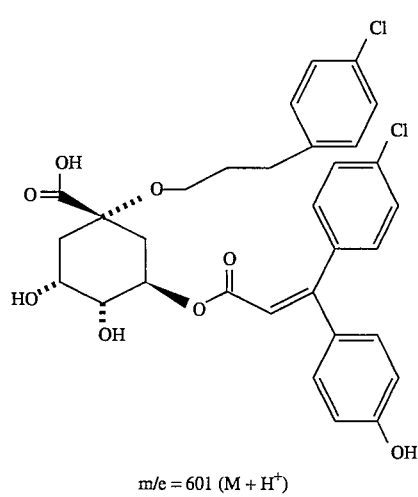
m/e = 601 (M + H⁺)
Example 82
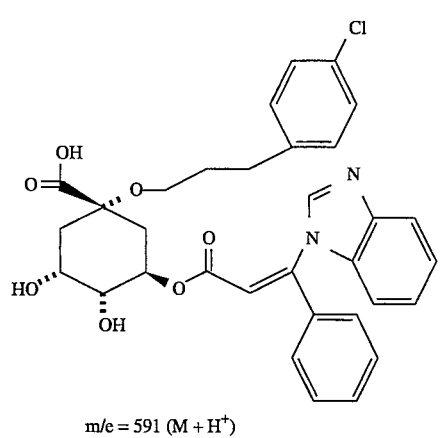
m/e = 591 (M + H⁺)

Example 83
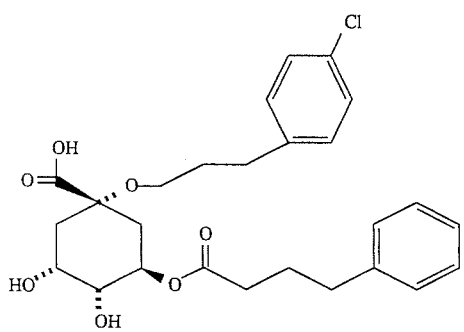
m/e = 491 (M + H⁺)
Example 84
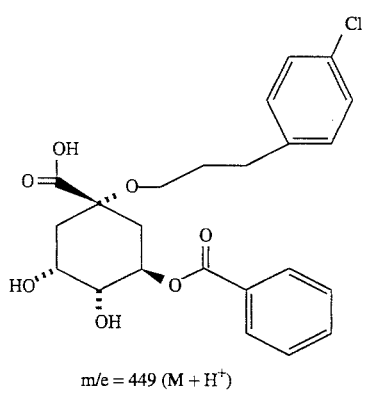
m/e = 449 (M + H⁺)
Example 85
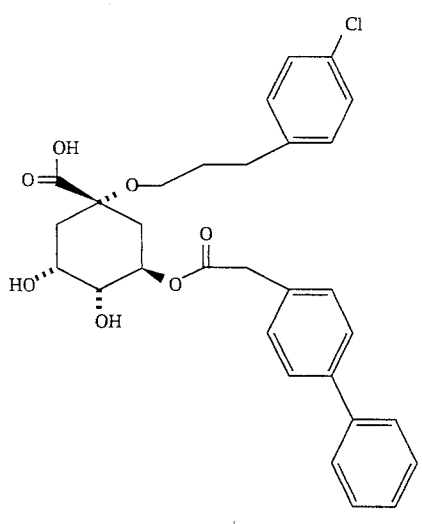
m/e = 539 (M + H⁺)
Example 86
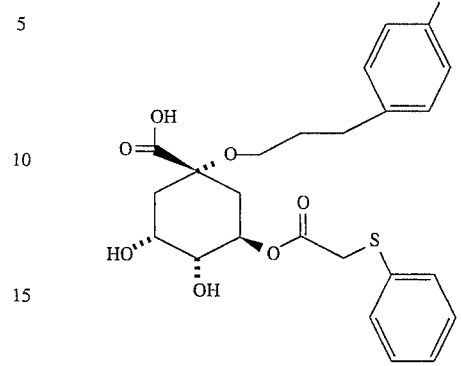
m/e = 495 (M + H⁺)
Example 87
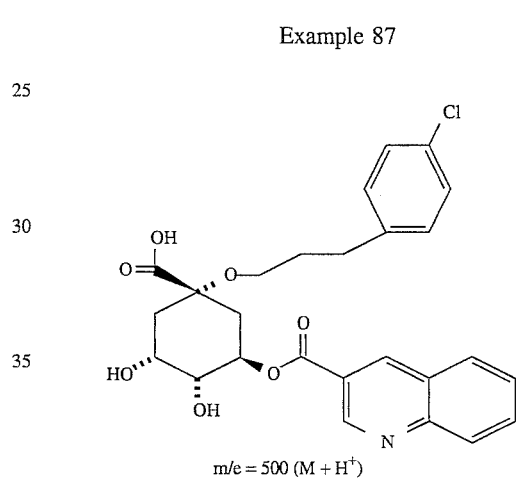
m/e = 500 (M + H⁺)
Example 88
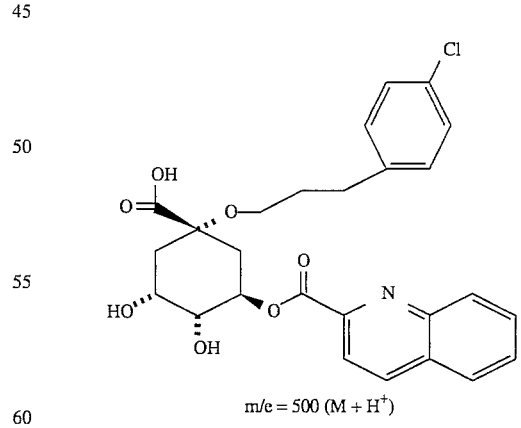
m/e = 500 (M + H⁺)

Example 89
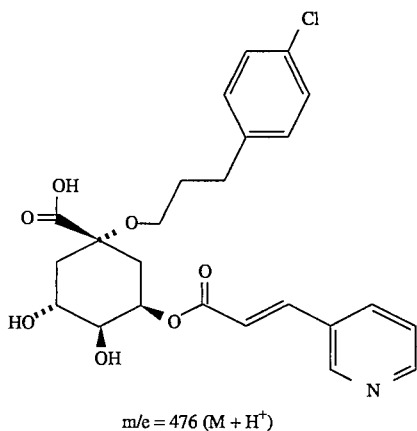
m/e = 476 (M + H⁺)
Example 90
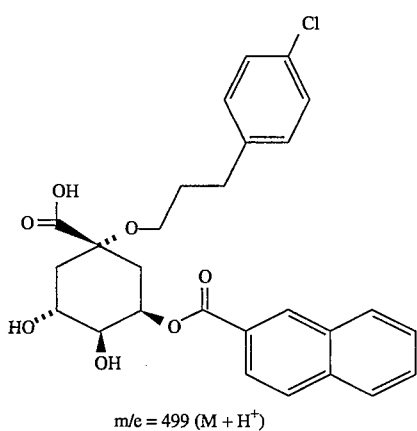
m/e = 499 (M + H⁺)
Example 91
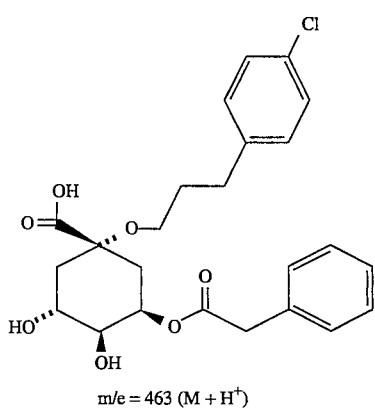
m/e = 463 (M + H⁺)
Example 92
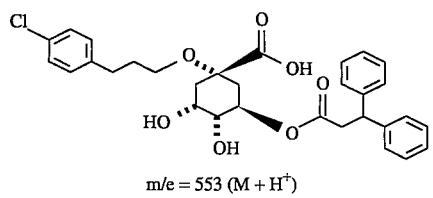
m/e = 553 (M + H⁺)
Example 93
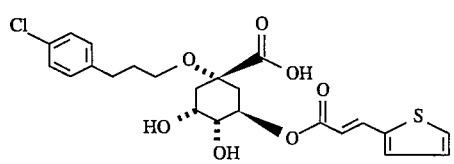
m/e = 481 (M + H⁺)
Example 94
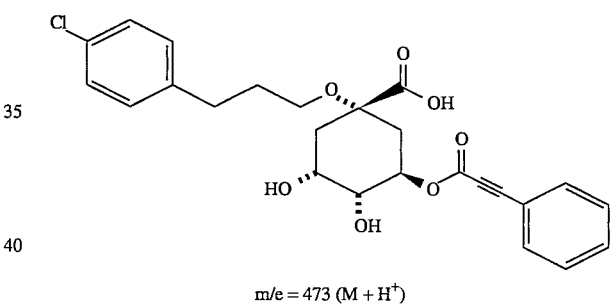
m/e = 473 (M + H⁺)
Example 95

Example 96
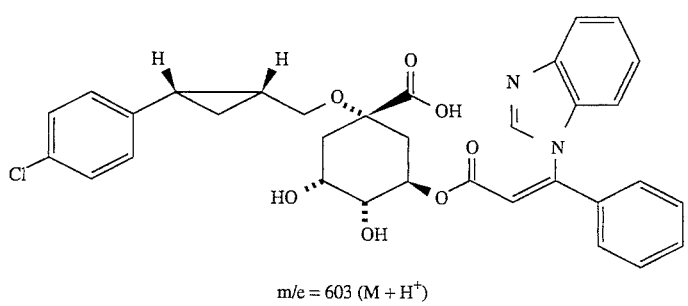
m/e = 603 (M + H⁺)
Example 97
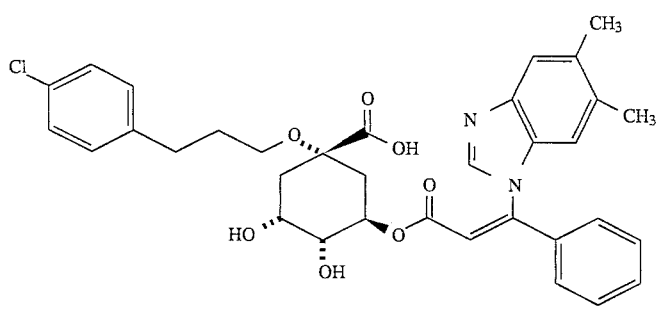
m/e = 619 (M + H⁺)
Example 98
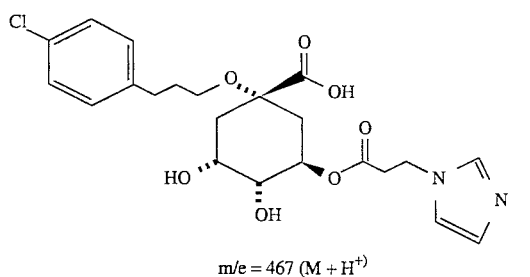
m/e = 467 (M + H⁺)
Example 99
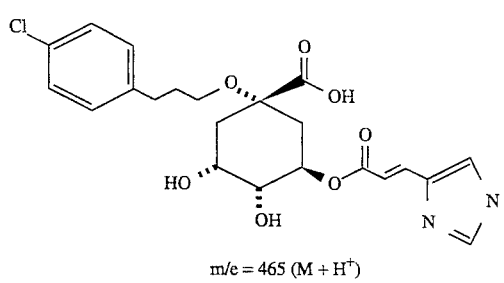
m/e = 465 (M + H⁺)
Example 100
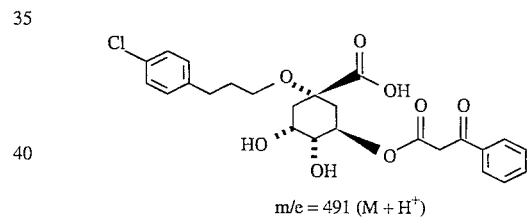
m/e = 491 (M + H⁺)
Example 101
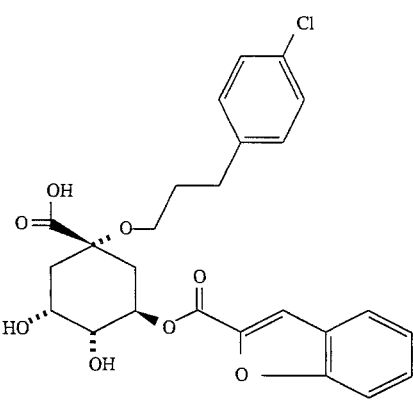
m/e = 489 (M + H⁺)

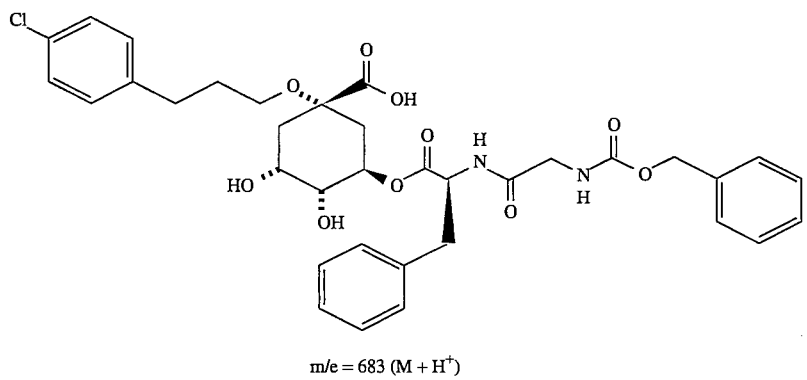
m/e = 683 (M + H⁺)
Example 102
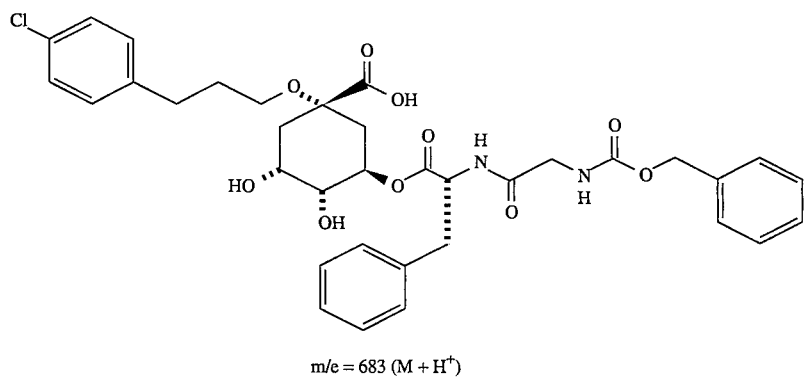
m/e = 683 (M + H⁺)
Example 103
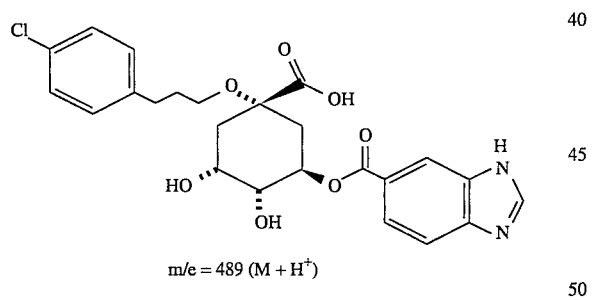
m/e = 489 (M + H⁺)
Example 104
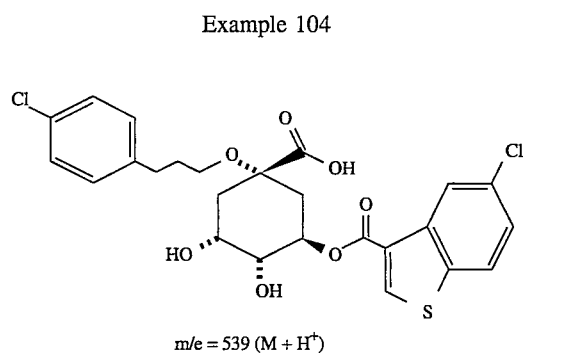
m/e = 539 (M + H⁺)
The compounds of the following examples were prepared by process C in analogy to the description before Example 45:
Example 105
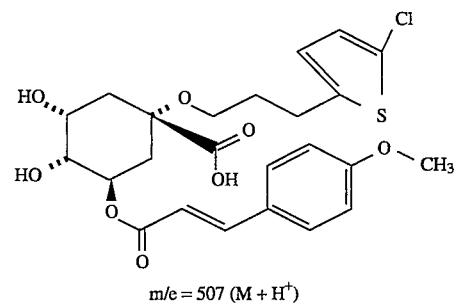
m/e = 507 (M + H⁺)

Example 106
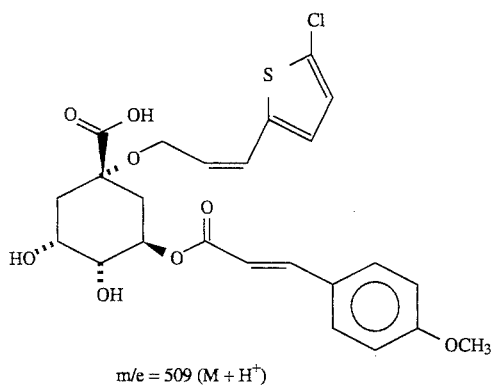
m/e = 509 (M + H⁺)
Example 107
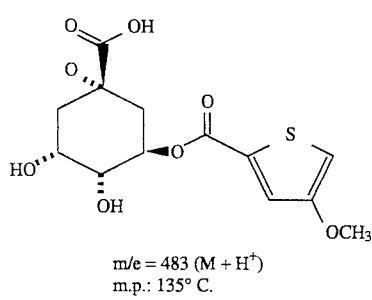
m/e = 483 (M + H⁺)
m.p.: 135° C.
Example 108
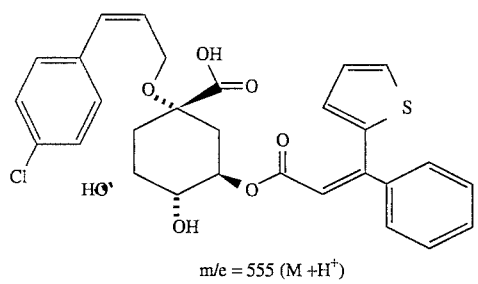
m/e = 555 (M +H⁺)
Example 109
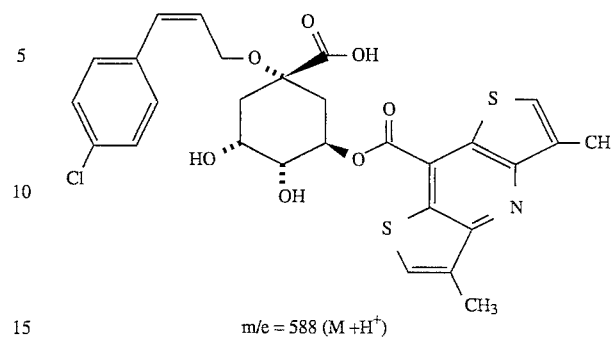
m/e = 588 (M +H⁺)
Example 110
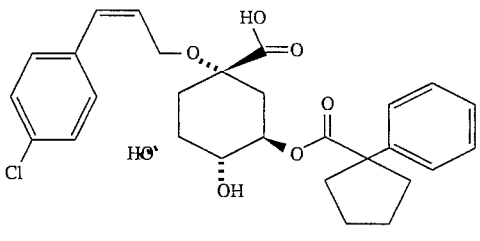
m/e = 515 (M +H⁺)
Example 111
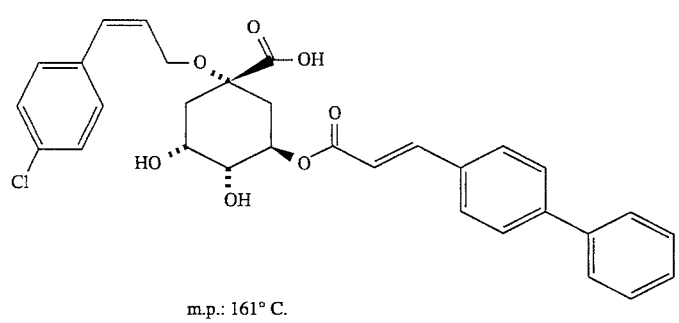
m.p.: 161° C.
Example 112

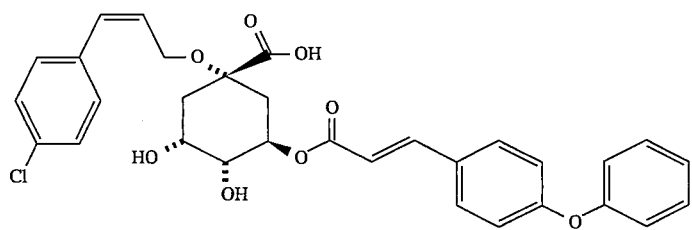
m/e = 565 (M + H⁺)
Example 113
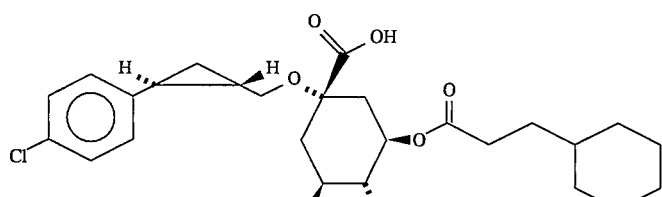
m/e = 495 (M + H⁺)
Example 114
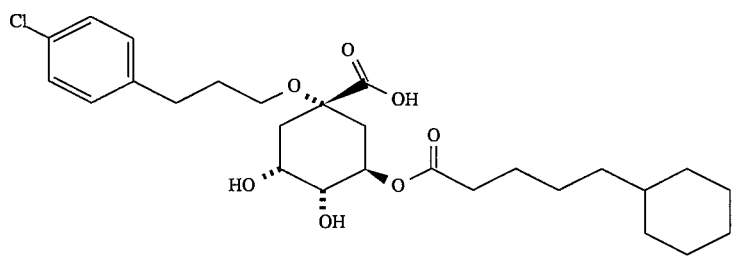
m/e = 511 (M + H⁺)
Example 115
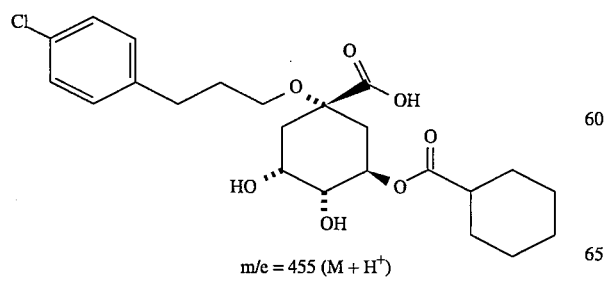
m/e = 455 (M + H⁺)
Example 116
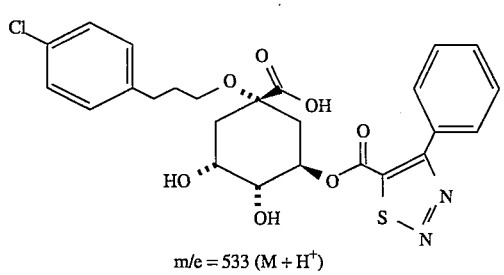
m/e = 533 (M + H⁺)

Example 117

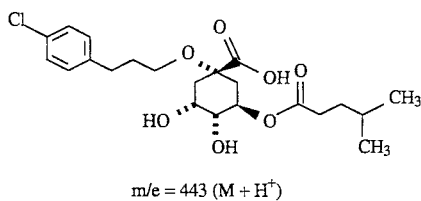

m/e = 443 (M + H$^+$)

Example 118

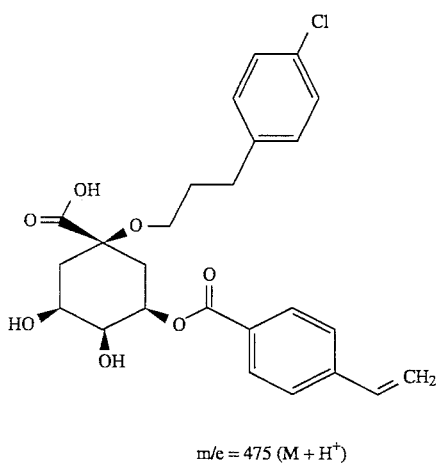

m/e = 475 (M + H$^+$)

Example 119

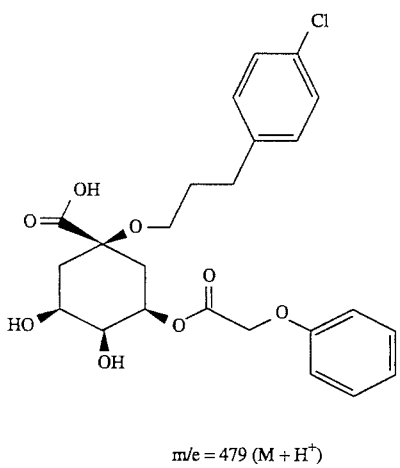

m/e = 479 (M + H$^+$)

Example 120

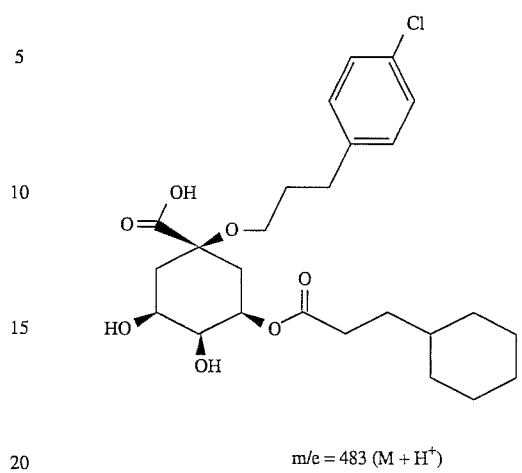

m/e = 483 (M + H$^+$)

We claim:
1. A cyclohexane derivative of the formula I

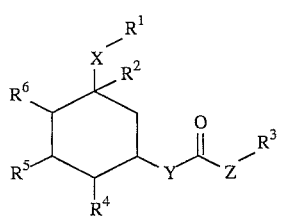

in which the radicals have the following meanings:

$R^1$ is CN, COOH, $C_1$-$C_4$-alkanoyl, $SO_3$-$C_1$-$C_4$-alkyl, $SO_3H$ or $SO_2NR^8R^9$;

$R^2$ is $C_1$-$C_{10}$-alkyl($R^{11}$)$_n$, O—$C_1$-$C_{10}$-alkyl($R^{11}$)$_n$, $C_2$-$C_{10}$-alkenyl($R^{11}$)$_n$, O—$C_3$-$C_{10}$-alkenyl($R^{11}$)$_n$, $C_2$-$C_{10}$-alkynyl($R^{11}$)$_n$, O—$C_3$-$C_{10}$-alkynyl($R^{11}$)$_n$, S—$C_1$-$C_{10}$-alkyl($R^{11}$)$_n$, S—$C_3$-$C_{10}$-alkenyl($R^{11}$)$_n$, S—$C_3$-$C_{10}$-alkynyl($R^{11}$)$_n$, NH—$C_1$-$C_{10}$-alkyl($R^{11}$)$_n$, NH—$C_3$-$C_{10}$-alkenyl($R^{11}$)$_n$ or NH—$C_3$-$C_{10}$-alkynyl($R^{11}$)$_n$, where $R^{11}$ is unsubstituted or substituted in each case by $R^{12}$;

$R^3$ is indolyl, imidazolyl, benzimidazolyl, quinolyl or tetrazolyl, the heteroaromatic system being unsubstituted or substituted one to three times, identically or differently, by F, Cl, Br, I, OH, $CF_3$, —$NO_2$, CN, $C_1$-$C_4$-alkoxy, $C_1$-$C_4$-alkyl, $NR^8R^9$, phenyl benzyl thienyl furyl, O-penyl or O-benzyl;

$R^{11}$ and $R^{13}$ are identical or different and are alkyl with 1 to 10 carbon atoms, cycloalkyl with 3–8 ring carbon atoms, phenyl, naphthyl, phenanthryl, thienyl, furyl or coumarinyl, the aromatic or heteroaromatic system being unsubstituted or substituted one to three times, identically or differently, by F, Cl, Br, I, OH, $CF_3$, —$NO_2$, CN, $C_1$-$C_4$-alkoxy, $C_1$-$C_4$-alkyl, $NR^8R^9$, phenyl, benzyl, thienyl, furyl, O-phenyl or O-benzyl;

R⁴, R⁵ and R⁶ are identical or different and are H, OH, a protected OH group, F, Cl or Br;

R⁷ is $C_1$–$C_4$-alkyl, phenyl or benzyl;

R⁸ and R⁹ are identical or different and are H, $C_1$–$C_4$-alkyl, $C_1$–$C_4$-alkanoyl, phenyl which is unsubstituted or substituted by F, Cl, Br, I, OH, O—$C_1$–$C_4$-alkyl, $CF_3$, —$NO_2$ or CN;

R¹² is phenyl, naphthyl, phenanthryl, thienyl, furyl or coumarinyl, the aromatic or heteroaromatic system being unsubstituted or substituted one to three times, identically or differently, by F, Cl, Br, I, OH, $CF_3$, —$NO_2$, CN, $C_1$–$C_4$-alkoxy, $C_1$–$C_4$-alkyl, $C_2$–$C_4$-alkenyl, $NR^8R^9$, phenyl, benzyl, thienyl, furyl, O-phenyl or O-benzyl;

X is $(CH_2)_m$, —CH=CH—, —C≡C—, —$CH_2$—O—$CH_2$-, —$CH_2$—S—$CH_2$— or

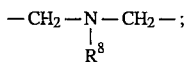

Y is $(CH_2)_m$, O, S or $NR^8$; Z is $(CH_2)_m$, S, O, S—$C_1$–$C_{10}$-alkyl, O—$C_1$–$C_{10}$-alkyl, CH=CH, CH=CF, CH=CCl, CH=CBr, $CH_2$—CO, $CH_2$—CHF, $CH_2$—CHCl, $CH_2$—CHBr, $CH_2$—CHI, $C_3$–$C_{10}$-cycloalkylene, $C_3$–$C_{10}$-cycloalkenylene, $COOR^7$, C≡C, CH=C($C_1$–$C_4$-alkyl), CH=C(CN), CH=C($NR^8R^9$), CH=C($C_1$–$C_4$-alkanoyl), CH=C(R¹³), $NR^8$, or $C_3$–$C_{10}$-cycloalkylene or $C_3$–$C_{10}$-cycloalkenylene in which 1 to 3 ring carbon atoms are replaced by sulfur or oxygen atoms, and when Y is oxygen,

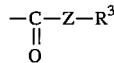

can together be an amino-acid residue selected from the group consisting of Ala, Arg, Asn, Asp, Cys, Gln, Glu, Gly, Ile, Leu, Lys, Phe, Pro, Ser, Thr, Tyr and their derivatives protected by conventional protective groups;

n is zero, 1 or 2;

m is zero, 1, 2, 3 or 4;

or a physiologically tolerated salt of the cyclohexane derivative of the formula I, with the exception of the compound in which R¹ is COOH; R² is O—$C_1$-alkyl($R^{11}$)$_n$ with n being 0; R³ is phenyl substituted in the 4-position with OH; R⁴ and R⁵ are both OH; R⁶ is hydrogen; X is $(CH_2)_m$ with m being 0; Y is oxygen; and Z is CH=CH.

2. A cyclohexane derivative or salt as claimed in claim 1, wherein the radicals in formula I have the following meanings:

R¹ to R⁹ R¹², X, Y, n and m have the meanings stated in claim 1;

R¹¹ and R¹³ are phenyl, naphthyl, phenanthryl, thienyl, furyl or coumarinyl, the aromatic or heteroaromatic system being unsubstituted or substituted one to three times, identically or differently, by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, O-phenyl or O-benzyl; and Z is $(CH_2)_m$, S, O, S—$C_1$–$C_{10}$-alkyl, CH=CH, CH=CF, CH=CCl, CH=CBr, $CH_2$—CO, $CH_2$—CHF, $CH_2$—CHCl, $CH_2$—CHBr, $CH_2$—CHI, $C_3$–$C_{10}$-cycloalkylene, $C_3$–$C_{10}$-cycloalkenylene, $COOR^7$, C≡C, CH=C($C_1$–$C_4$-alkyl), CH=C(CN), CH=C($NR^8R^9$), CH=C($C_1$–$C_4$-alkanoyl), CH=C(R¹³) or $NR^8$ and when Y is oxygen,

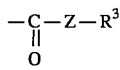

can together be an amino-acid residue selected from the group consisting of Ala, Arg, Asn, Asp, Cys, Gln, Glu, Gly, Ile, Leu, Lys, Phe, Pro, Ser, Thr, Tyr and their derivatives protected by conventional protective groups, or a physiologically tolerated salt of said cyclohexane derivative.

3. A cyclohexane derivative or salt as claimed in claim 1, wherein R¹ in formula I is CN, COOH or $C_1$–$C_4$-alkanoyl.

4. A cyclohexane derivative or salt as claimed in claim 1, wherein the radicals in formula I have the following meanings:

R¹ to R⁹ and R¹¹ to R¹³ have the meanings stated in claim 1;

R² is O—$C_1$–$C_{10}$-alkyl(R¹¹)$_n$ (n=0,1,2), where the alkyl moiety is unbranched or branched or cyclic, and one of the $CH_2$ groups is unchanged or replaced by O, and R¹¹ is unsubstituted or substituted by R¹², and when n=2 the two R¹¹ radicals are identical or different, O—$C_3$–$C_{10}$-alkenyl(R¹¹)$_n$ (n=0,1,2), where the alkenyl moiety is unbranched, branched or cyclic, one of the $CH_2$ groups is unchanged or replaced by O, S, SO, $SO_2$ or $NR^8$, and is unsaturated one or more times, and R¹¹ is unsubstituted or substituted by R¹², and when n=2 the two R¹¹ radicals are identical or different, or O—$C_3$–$C_{10}$-alkynyl(R¹¹)$_n$ (n=0,1,2), where the alkynyl moiety is unbranched, branched or cyclic and is unsaturated one or more times, and one of the $CH_2$ groups is unchanged or replaced by O, S, SO, $SO_2$ or $NR^8$, and R¹¹ is unsubstituted or substituted by R¹², and when n=2 the two R¹¹ radicals are identical or different;

X is $(CH_2)_m$ (m=0,1,2,3,4), CH=CH, C≡C, $CH_2OCH_2$ or $CH_2SCH_2$;

Y is $(CH_2)_m$ (m=0,1,2,3,4), O, S or $NR^8$;

Z is $(CH_2)_m$ (m=0,1,2,3,4), S, O, S—$C_1$–$C_{10}$-alkyl, (unbranched or branched), CH=CH, CH=CF, CH=CCl, CH=CBr, $CH_2$—C(O), $CH_2$—CHF, $CH_2$—CHCl, $CH_2$—CHBr, $CH_2$—CHI, $C_3$–$C_{10}$-cycloalkylene, $C_3$–$C_{10}$-cycloalkenylene, $COOR^7$, C≡C, CH=C($C_1$–$C_4$-alkyl) (unbranched or branched), CH=C(CN), CH=C(R¹³) or $NR^8$.

5. A method of treatment of diseases associated with an increased activity of the glucose-6-phosphatase system, which comprises administering to a host in need thereof an effective amount of a compound as claimed in claim 1.

6. A method of treatment of diseases associated with an increased hepatic glucose production, which comprises administering to a host in need thereof an effective amount of a compound as claimed in claim 1.

7. A method of treatment of type II diabetes (non-insulin-dependent or adult-onset diabetes), which comprises administering to a host in need thereof an effective amount of a compound as claimed in claim 1.

8. A method of production of pharmaceuticals for the treatment of type II diabetes and other disorders characterized by an increased output of glucose from the liver or an increased activity of the glucose-6-phosphatase system, which comprises combining an effective amount of a compound as claimed in claim 1 with a pharmaceutically acceptable carrier.

9. A pharmaceutical containing a compound as claimed in claim 1 and a pharmaceutically acceptable carrier.

10. A pharmaceutical containing a compound as claimed in claim 2 and a pharmaceutically acceptable carrier.

11. A cyclohexane derivative selected from the group consisting of:

{1S,3R,4R,5S}-1-(4-chlorophenylpropyl)oxy-3-{(E)-3-(4-hydroxyphenyl)-2-propenoyl}oxy-4,5 -dihydroxycyclohexanecarboxylic acid;

{1S,3R,4R,5S}-1-((E)-3-(4-chlorophenyl)-2-propenyl)oxy-3-{(E)-3-(4-hydroxyphenyl)-2-propenoyl}oxy-4,5-dihydroxycyclohexanecarboxylic acid;

{1S,3R,4R,5S}-1-((E)-3-(2-chlorophenyl)-2-propenyl)oxy-3-{(E)-3-(4-hydroxyphenyl)-2-propenoyl}oxy-4,5-dihydroxycyclohexanecarboxylic acid;

{1S,3R,4R,5S}-1-(3-(4-chlorophenyl)propyl)oxy-3-{3-(4-methoxyphenyl)propyl}oxy-4,5-dihydroxycyclohexanecarboxylic acid;

{1S,3R,4R,5S}-1-(2-(4-chlorophenyl-1-cyclopropylenemethyl)oxy-3-{(E)-3-(4 -hydroxyphenyl)-2-propenoyl}oxy-4,5-dihydroxycyclohexanecarboxylic acid;

sodium {1S,3R,4R, 5S}-1-((Z)-3-(4-chlorophenyl))-2-propenyl)oxy- 3-{(E)-3-(4-hydroxyphenyl)propoyl}oxy-4-phenylmethyloxy-5 -dihydroxycyclohexanecarboxylate;

and a compound of the formulae:

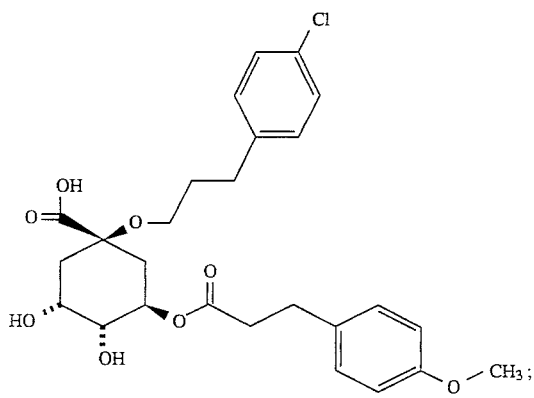

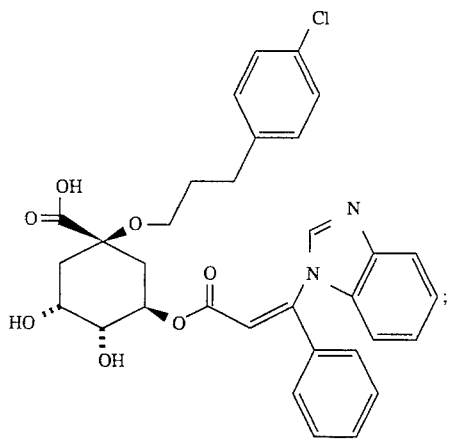

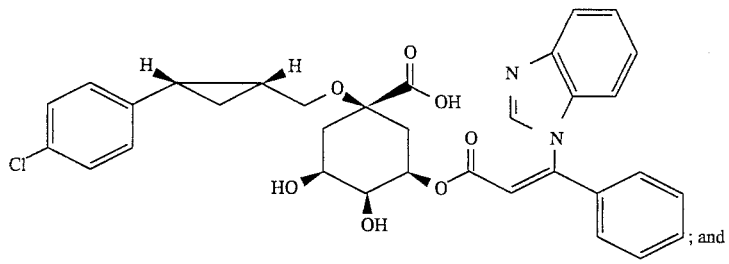

-continued
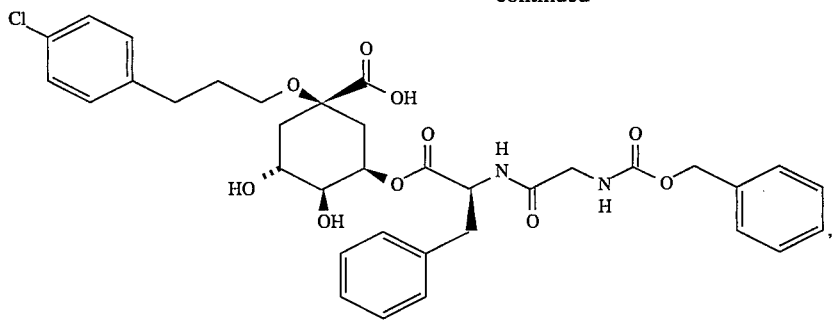
or a physiologically tolerated salt of said cyclohexane derivative.
* * * * *